US009050033B2

(12) United States Patent
Yoneyama et al.

(10) Patent No.: US 9,050,033 B2
(45) Date of Patent: Jun. 9, 2015

(54) INFORMATION PROCESSING FOR A BODY MOTION SIGNAL

(75) Inventors: Mitsuru Yoneyama, Kanagawa (JP); Hiroshi Mitoma, Tokyo (JP)

(73) Assignee: MITSUBISHI CHEMICAL CORPORATION, Tokyo (JP)

( * ) Notice: Subject to any disclaimer, the term of this patent is extended or adjusted under 35 U.S.C. 154(b) by 0 days.

(21) Appl. No.: 13/433,878

(22) Filed: Mar. 29, 2012

(65) Prior Publication Data
US 2012/0209149 A1 Aug. 16, 2012

Related U.S. Application Data

(63) Continuation of application No. PCT/JP2010/066098, filed on Sep. 16, 2010.

(30) Foreign Application Priority Data

Sep. 30, 2009 (JP) ................................. 2009-228442

(51) Int. Cl.
*A61B 5/103* (2006.01)
*A61B 5/11* (2006.01)
*A61B 5/00* (2006.01)

(52) U.S. Cl.
CPC .............. *A61B 5/112* (2013.01); *A61B 5/1123* (2013.01); *A61B 5/4082* (2013.01); *A61B 5/7242* (2013.01)

(58) Field of Classification Search
USPC .............. 33/511, 512; 434/247; 600/587, 595
See application file for complete search history.

(56) References Cited

U.S. PATENT DOCUMENTS

| 7,245,960 | B2 | 7/2007 | Yasushi et al. | |
| 7,983,872 | B2 | 7/2011 | Makino et al. | |
| 2002/0156392 | A1* | 10/2002 | Arai et al. | 600/546 |
| 2004/0044292 | A1* | 3/2004 | Yasushi et al. | 600/509 |
| 2006/0244744 | A1* | 11/2006 | Kandori et al. | 345/418 |

(Continued)

FOREIGN PATENT DOCUMENTS

| CN | 1530880 A | 9/2004 |
| JP | 2000-166877 | 6/2000 |

(Continued)

OTHER PUBLICATIONS

International Search Report issued on Jan. 11, 2011 for PCT/JP2010/066098 filed on Sep. 16, 2010 with English Translation.
International Written Opinion issued on Jan. 11, 2011 for PCT/JP2010/066098 filed on Sep. 16, 2010.
Chinese Office Action and Search Report issued Oct. 8, 2013 in corresponding Chinese Appln. No. 201080041791.2 (with English translation).
Extended European Search Report issued on Apr. 8, 2015 in European Patent Application No. 10820378.7.

(Continued)

*Primary Examiner* — Sean Dougherty
*Assistant Examiner* — Daniel Cerioni
(74) *Attorney, Agent, or Firm* — Oblon, McClelland, Maier & Neustadt, L.L.P.

(57) ABSTRACT

An information processing method includes the following steps: applying a pattern matching process on the body motion signal information, and extracting rhythm cycle candidate waves which are rhythm cycle candidates related to the rhythmic motion; performing −1 or more times integration on the body motion signal information to obtain a motion trajectory, and performing coarse-graining on the motion trajectory to produce an auxiliary wave; superimposing the rhythm cycle candidate waves which are extracted in the process of extracting the cycle candidate waves, on the obtained auxiliary wave, and selecting a cycle of a rhythm cycle candidate wave which has a peak in the auxiliary wave, as a true cycle; and finally obtaining a result of the processing.

38 Claims, 22 Drawing Sheets

(56) References Cited

U.S. PATENT DOCUMENTS

| 2008/0238414 | A1 | 10/2008 | Miyashita et al. | |
| 2009/0082681 | A1* | 3/2009 | Yokoyama et al. | 600/509 |
| 2009/0192418 | A1* | 7/2009 | Miyashita et al. | 600/595 |
| 2009/0240461 | A1* | 9/2009 | Makino et al. | 702/141 |
| 2010/0087752 | A1* | 4/2010 | Li et al. | 600/561 |

FOREIGN PATENT DOCUMENTS

| JP | 2004-089314 | 3/2004 |
| JP | 2007-244495 | 9/2007 |
| JP | 2008-154733 | 7/2008 |
| JP | 2008-246126 | 10/2008 |
| JP | 2009-291379 | 12/2009 |

OTHER PUBLICATIONS

M. Costa, et al., "Multiscale Entropy Analysis of Human Gait Dynamics", Physica A: Statistical Mechanics and Its Applications, vol. 330, No. 1-2, Dec. 1, 2003, pp. 53-60.

Sekine, M. et al., "Investigating Body Motion Patterns in Patients With Parkinson's Disease Using Matching Pursuit Algorithm", Medical and Biological Engineering and Computing, Springer, Heildelberg, DE, vol. 42, No. 1, Jan. 1, 2004.

Wajid Aziz et al., "Genetically Optimized Hybrid Gait Dynamics Classifier", Emerging Technologies, 2006. ICET '06. International Conference O N, IEEE, PI, Jan. 1, 2006, pp. 765-770.

* cited by examiner

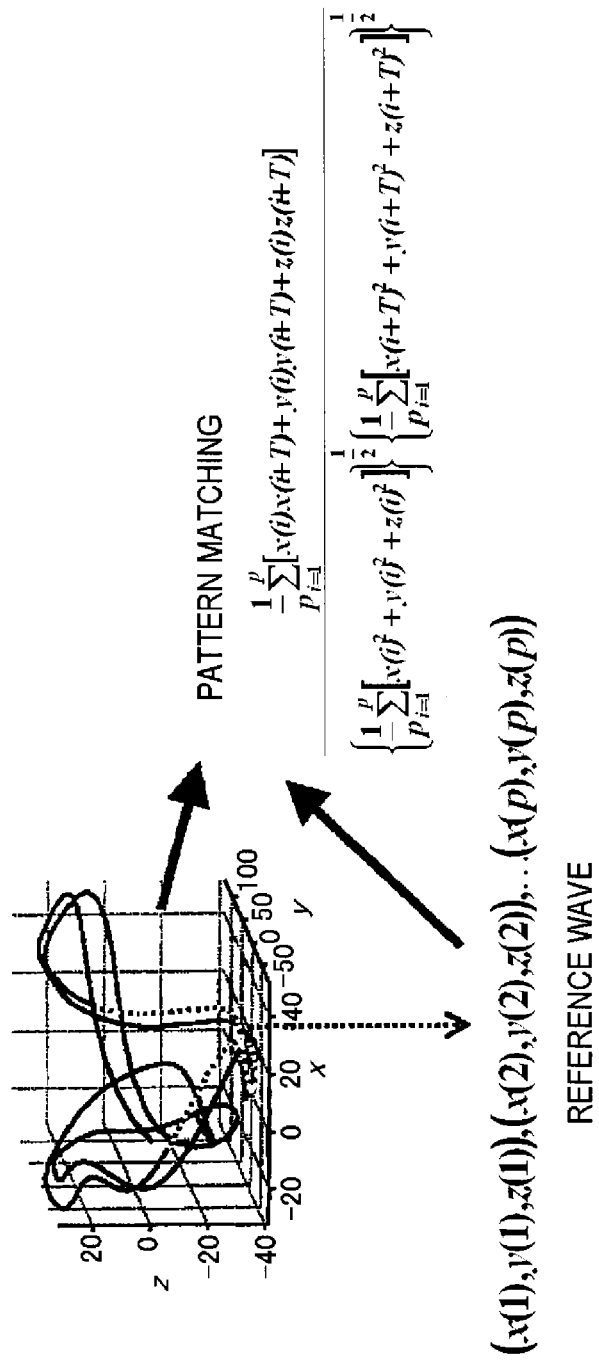

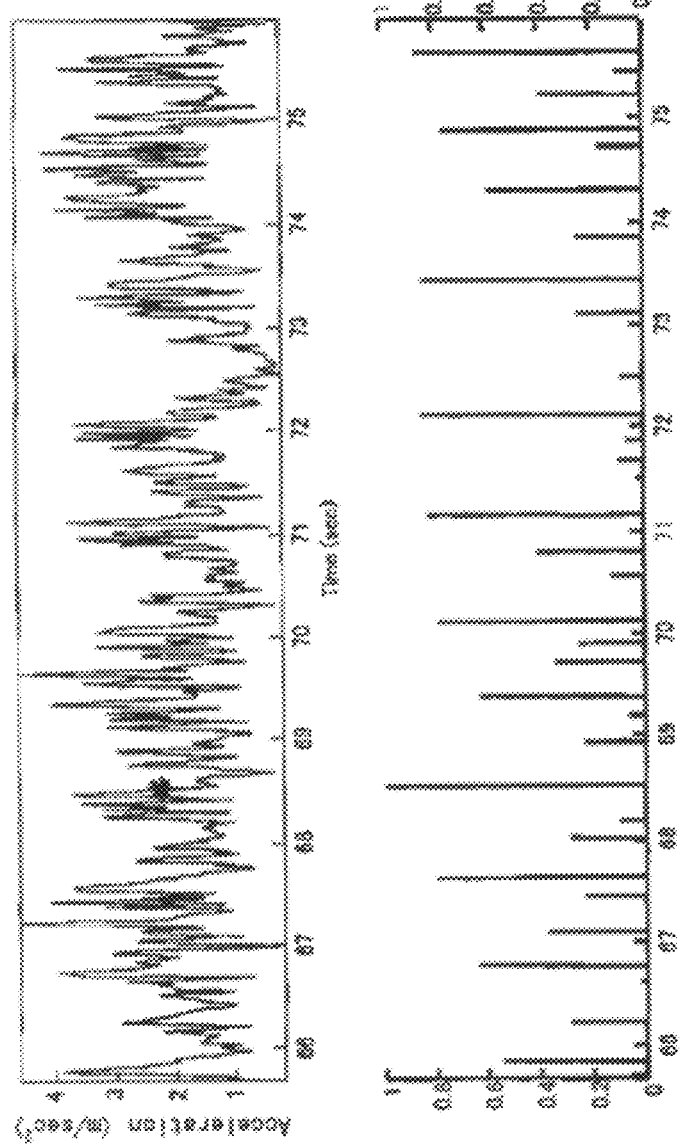

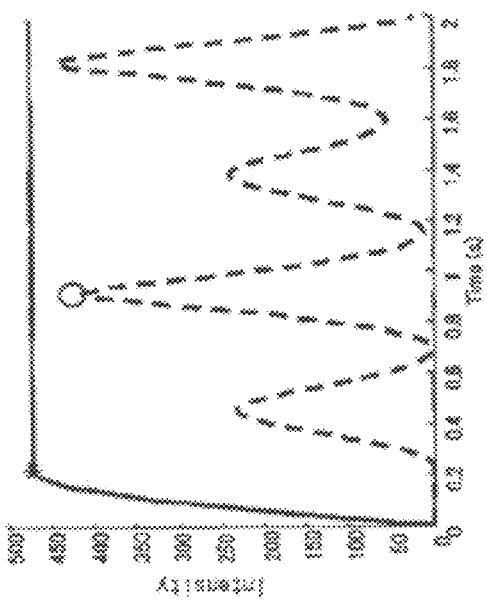
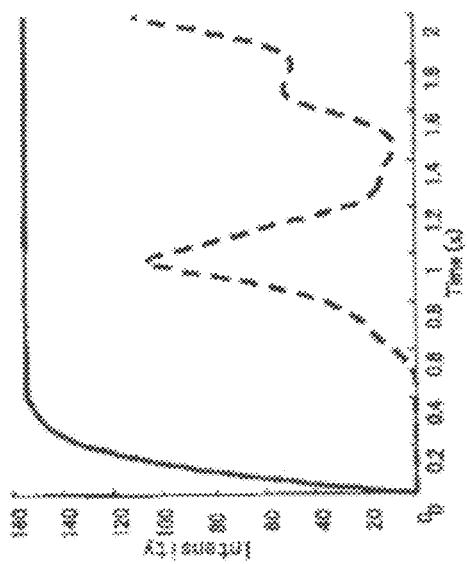
FIG. 7A
FIG. 7B

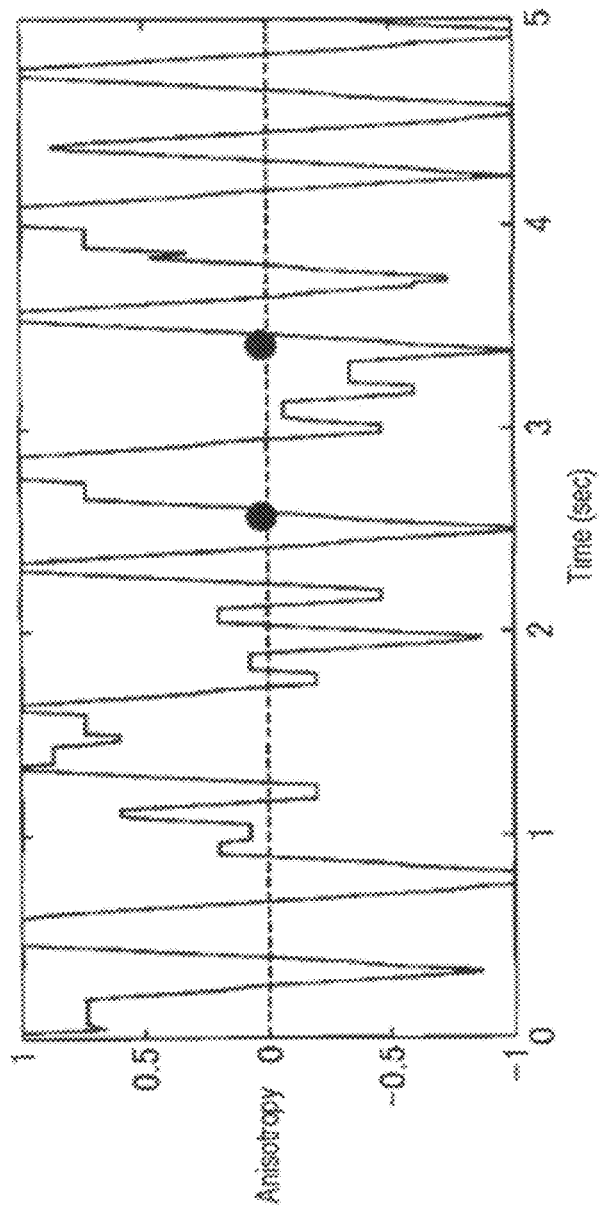

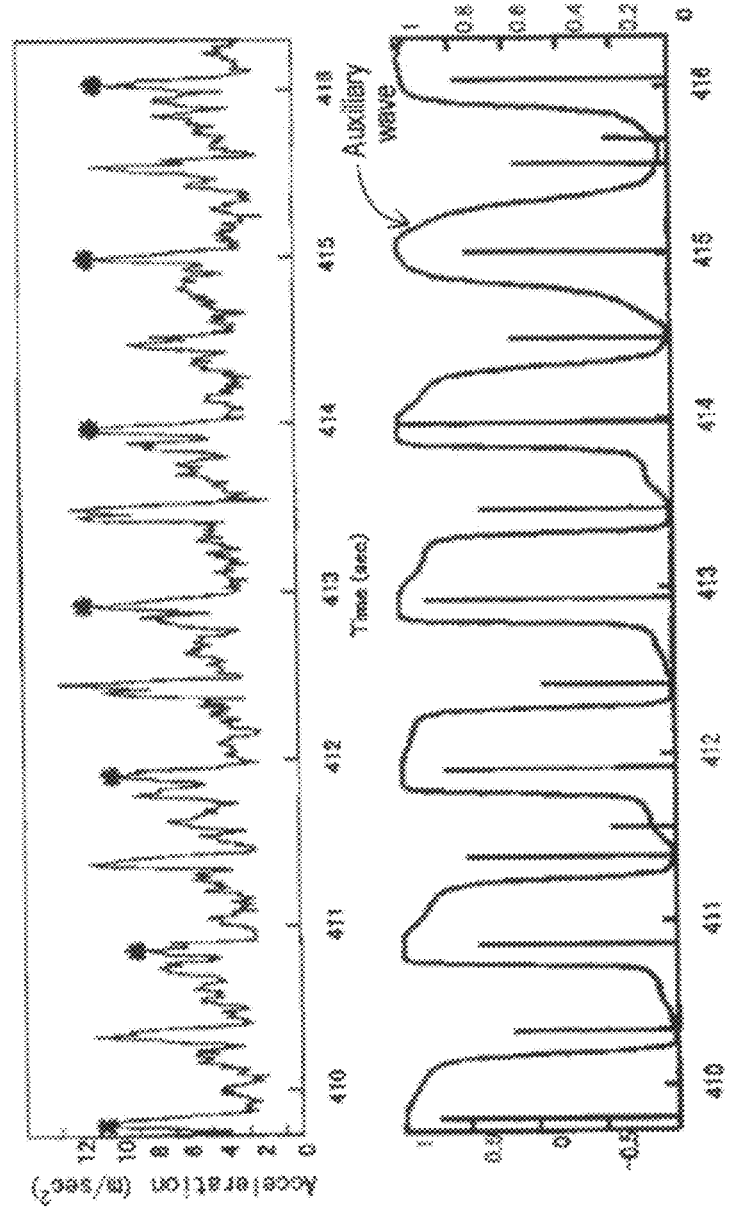

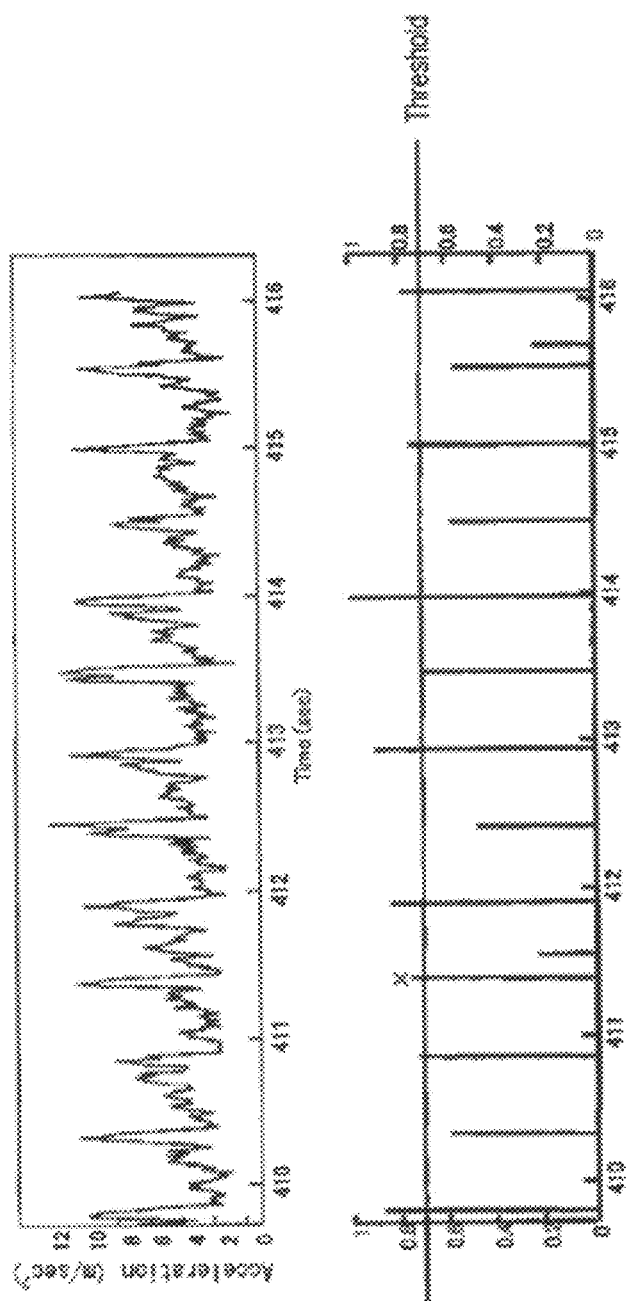

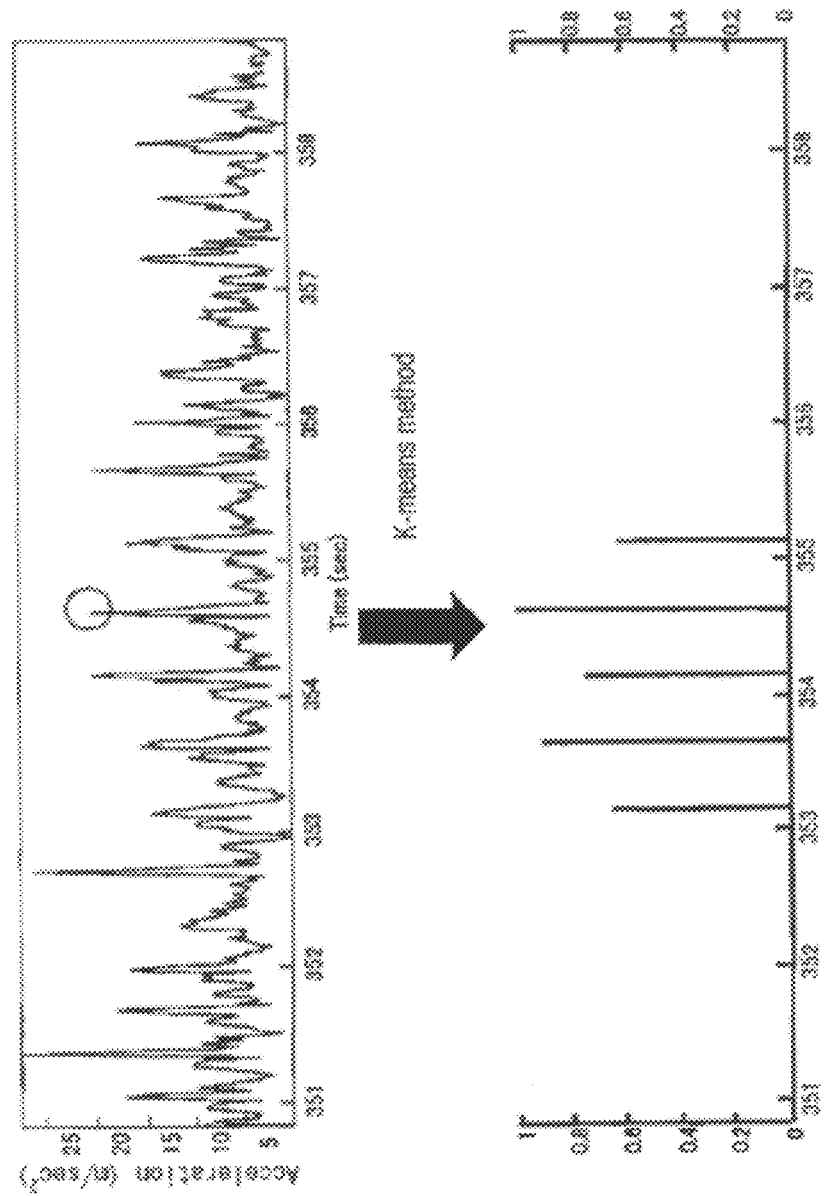

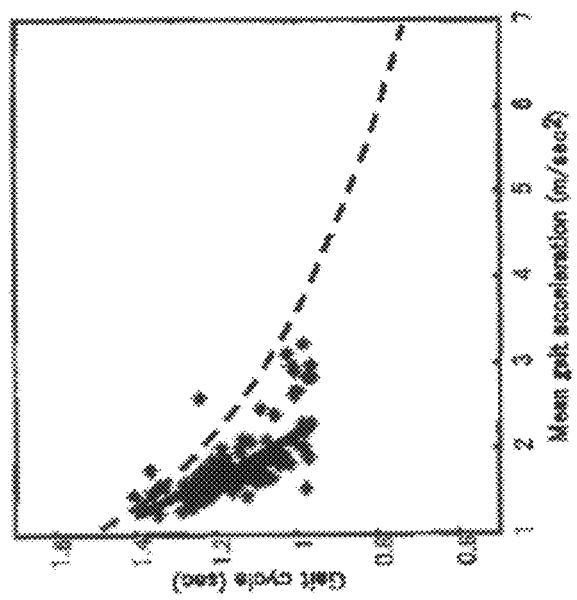
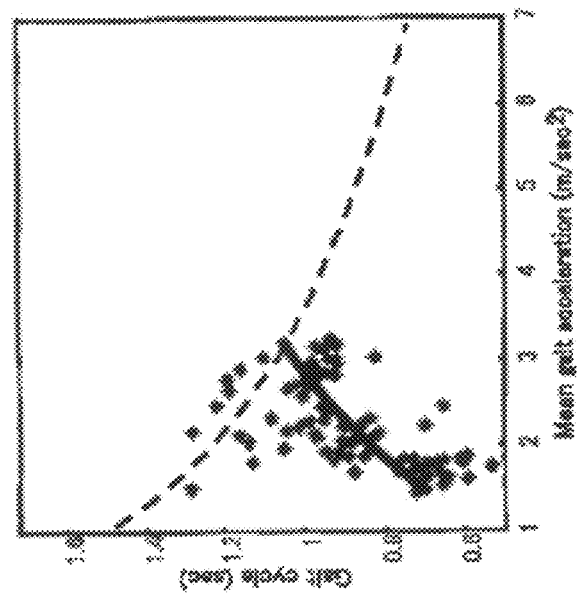
FIG. 21A
FIG. 21B

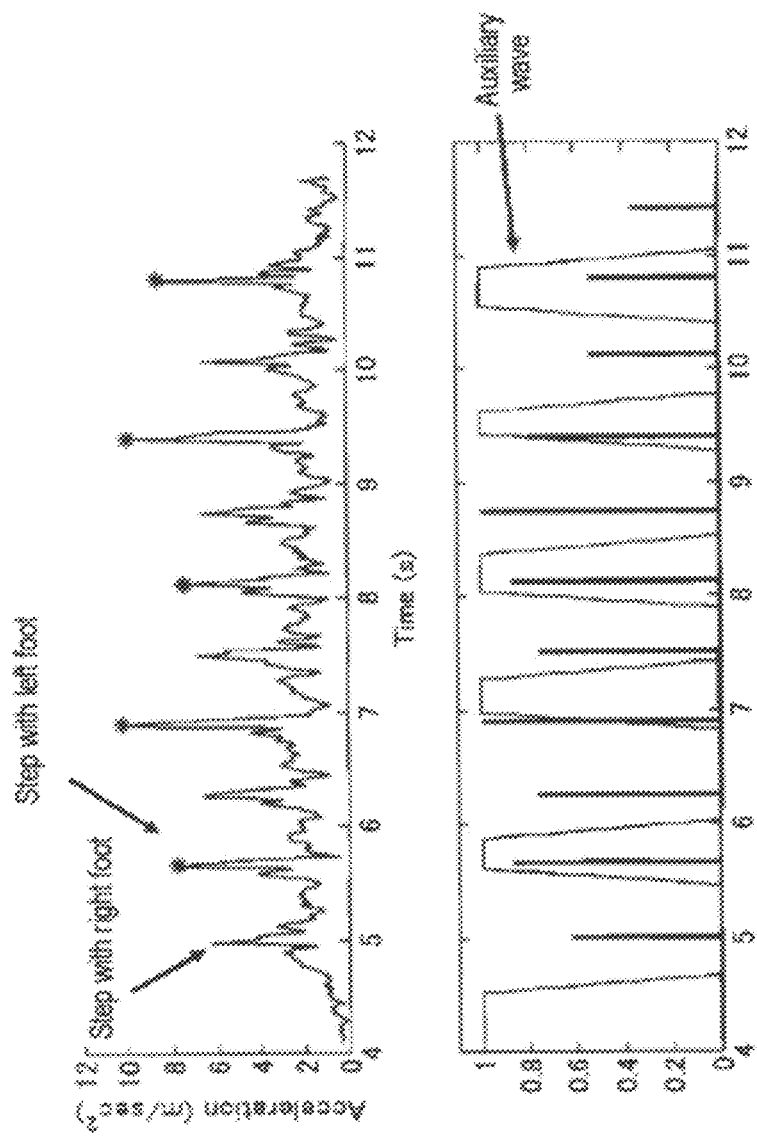

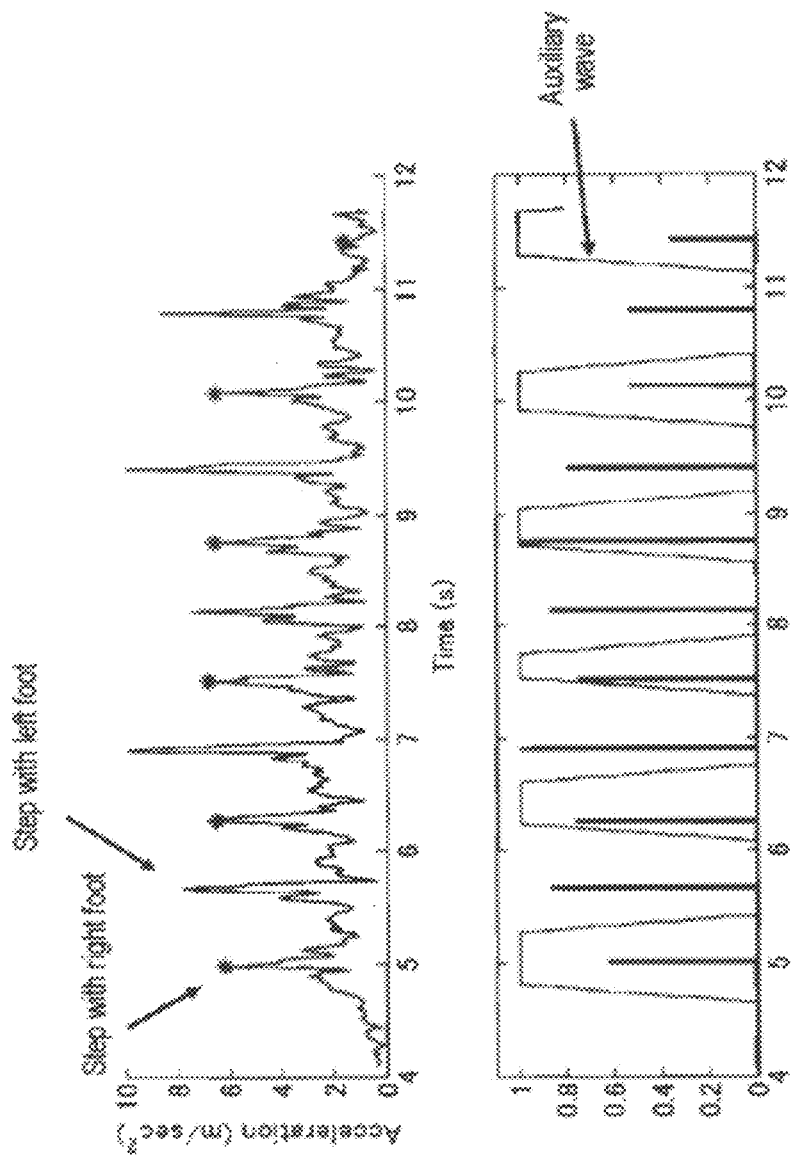

INFORMATION PROCESSING FOR A BODY MOTION SIGNAL

CROSS REFERENCE TO RELATED APPLICATION

This application is a continuation of PCT application No. PCT/JP2010/066098, which was filed on Sep. 16, 2010 based on Japanese Patent Application (No. 2009-228442) filed on Sep. 30, 2009, the contents of which are incorporated herein by reference. Also, all the references cited herein are incorporated as a whole.

BACKGROUND OF THE INVENTION

1. Technical Field

The present invention relates to an information processing method for a body motion signal, an information processing system for a body motion signal, an information processing apparatus for a body motion signal, displaying apparatus, a displaying method, a recording medium on which a program is recorded, a program, a body motion signal detecting apparatus, a method of detecting a body motion signal, an outputting apparatus, an outputting method, a diagnosing method of diagnosing an illness, a diagnosing system for diagnosing an illness, and a diagnosing apparatus for diagnosing an illness which are preferably used in, for example, evaluation of the severity or state change of Parkinson's disease.

2. Background Art

In Japan, the prevalence rate of Parkinson's disease reaches 100 to 150 per 100,000. With respect to Parkinson's disease, it is impossible to observe a notable finding in diagnostic imaging of the brain. Therefore, the Yahr rating scale, the UPDRS, and the like are used for classification and evaluation of Parkinson's disease patients.

However, these methods involve subjective evaluations of the doctor, the patient, and the like, and hence it is sometimes difficult to perform quantitative and objective determination. Among symptoms of Parkinson's disease, tremor, akinesia, and rigidity are known as three main symptoms. All of these symptoms do not always appear during, for example, diagnosis by a doctor.

Furthermore, Parkinson's disease is characterized also by abnormality gait, and presents various symptoms such as a slow gait, a small-step gait, and the like depending on the severity or the time of a day.

Information related to such abnormality gait is empirically known only by a complaint of the patient and his/her family. As it now stands, therefore, it is very difficult for a medical specialist to diagnose Parkinson's disease and know the pathological condition, only by examinations in an outpatient visit and a round in the hospital.

In the past, therefore, a system for non-invasively measuring Parkinson's disease has been proposed. An apparatus which analyzes the gait rhythm of a subject to early detect a reduction of the neurological system function has been proposed by the present inventors (see JP-A-2000-166877).

According to the invention disclosed in JP-A-2000-166877, it is possible to determine whether the subject suffers from a neurological disease such as Parkinson's disease or not. However, it is difficult to finely evaluate the severity or change of the pathological condition.

In order to evaluate Parkinson's disease, the gait rhythm of a subject must be always correctly measured. However, the time period which is required for one step in human walking (the time period ranging from a landing of a same foot, e.g., the right foot to the next landing of the right foot, hereinafter referred to as the gait cycle) is not constant even in a healthy subject, and always fluctuates.

In order to, considering this fluctuation, correctly obtain the cycle of each step (one cycle), for example, the peak position must be correctly detected from a time-series signal of the absolute value of an acceleration signal. When an objective phenomenon or waveform is to be extracted from a noisy signal as described above, pattern matching such as autocorrelation or cross-correlation is conventionally often used.

Specifically, a method of detecting a peak corresponding to an R wave from a correlation value between an electrocardiogram waveform and template data is disclosed (see JP-A-2004-89314). However, a way how to determine an actual peak from the correlation value is not disclosed.

Moreover, a method of deciding a peak position from matching between a vertical component of an acceleration and a predetermined waveform has been disclosed (see JP-A-2007-244495). However, the disclosure is made in obscure description that a peak is set in the case where the degree of similarity is high, and the method is not described in detail.

Moreover, preconditions that band division of a signal is performed in the determination of a peak and the pass bandwidth in the vertical direction is set to 2 to 4 Hz, and that a threshold of an energy ratio is disposed are set. Therefore, the method cannot cope with the case where the way or cycle of walking is suddenly largely changed. Moreover, the gravitational component of an acceleration is used for determining the vertical direction, and hence the method cannot cope with a process of a signal from an acceleration sensor which does not measure the gravitational component.

Furthermore, a method which can accurately detect the gait rhythm has been proposed (see JP-A-2008-154733). However, the method has a limitation in that the electric field of the human body must be measured. Moreover, the duration and frequency band for detecting the gait must be set as preconditions.

Also a diagnosis apparatus for Parkinson's disease in which a signal obtained from an acceleration sensor is analyzed has been proposed (see JP-A-2009-291379). JP-A-2009-291379 discloses that feature points are extracted from the waveform of the rhythm, and the time interval between adjacent feature points is set as the cycle of the rhythm. However, a specific method of correctly extracting feature points is not clearly described.

In a measurement method for evaluation of Parkinson's disease, from a further practical view point, the position where a device is attached is not fixed, and the method is requested to cope with a situation where the position of the device is changed or shifted with the elapse of time. In such a case, a signal is susceptible to influence of noises. Also in the case where, due to an illness such as Parkinson's disease, the walk cannot be forcefully performed or is accompanied by shakes, the gait waveform is disturbed.

Moreover, there is a case where, due to an illness such as Parkinson's disease, the gait cycle is suddenly prolonged or shortened during gait. Such a case occurs when a patient runs down stairs. Usually, the gait cycle is about 1 sec., and sometimes suddenly shortened to 0.5 sec. or shorter or prolonged to 2 sec. or longer.

Also a Parkinson's disease patient sometimes shows freezing of gait in which the gait cycle is suddenly shortened. Accurate detection of freezing of gait is very important for knowing the pathological condition. In the case where the gait pace is rapidly changed, it is difficult for a spectrum analyzing method in which an average cycle of a signal is obtained, to distinguish whether the obtained cycle is caused by a gait of a cycle of 0.5 sec. or by the time interval of 0.5 sec. between the right and left feet in the normal gait of a cycle of 1 sec.

When preconditions that the gait cycle is in the vicinity of 1 sec. are set as conventionally performed in the above-described spectrum analyzing method, the method cannot cope with a gait which is largely deviated from the preconditions.

In addition to Parkinson's disease, furthermore, with respect to various illnesses or diseases which cause impairment in the nervous system, muscles, skeleton, and the like related to a gait, such as stroke, spinal cord injury, cerebral palsy, myelodysplasia, muscular dystrophy, osteoarthritis, rheumatoid arthritis, multiple sclerosis, alcoholic intoxication, dementia, and hydrocephalus, it is desired to adequately know the pathological condition based on the gait rhythm.

SUMMARY OF THE INVENTION

From the above situation, a method which always accurately measures the gait rhythm of the subject including a patient of Parkinson's disease or the like for a long time period (for example, one day or longer) without imposing a load on the subject, i.e., a method which accurately detects feature points such as peak positions from a time-series signal of a noisy body motion signal of the subject is requested.

The present invention has been worked out in view of such a problem. It is an object of the present invention to continuously monitor the subject without imposing a load on the subject and always accurately measure the gait rhythm of the subject, or namely accurately detect feature points such as peak positions from a time-series signal of a body motion signal of the subject.

Furthermore, also accurate evaluation of the severity or change of the pathological condition of an illness or disease such as Parkinson's disease by always accurately measuring the gait rhythm of the subject is regarded as one object of the present invention.

The present inventors found that, according to their dedicated research, it is possible to accurately detect feature points such as peak positions from a time-series signal of a noisy body motion signal of the subject, for example, by measuring non-invasively and continuously a repetitive rhythmic motion of a human body, obtaining body motion signal information and performing a unique analysis on the body motion signal information. Further, the present inventors found that it is possible to find and evaluate the pathological condition such as Parkinson's disease without constraint by an attaching position of the device and preconditions for the analysis by performing a unique analysis on the body motion signal information, and have reached achieving the present invention.

Namely, overview of the present invention is shown as follows:

An information processing method for a body motion signal in an information processing apparatus for performing information processing on body motion signal information which is obtained by an operation in which a subject carries a body motion signal detecting apparatus having a body motion signal detection section that measures non-invasively and continuously at least a repetitive rhythmic motion of a human body and for extracting a result obtained in the information processing, the information processing including following steps of (1) to (3):

(1) a cycle candidate extracting step of applying a pattern matching process on the body motion signal information, and extracting a rhythm cycle candidate wave as rhythm cycle candidates related to the rhythmic motion;

(2) an auxiliary-wave producing step of performing −1 or more times integration on the body motion signal information to obtain a motion trajectory, and performing coarse-graining on the motion trajectory to produce an auxiliary wave; and (3) a cycle selecting step of superimposing the rhythm cycle candidate wave which is extracted in the cycle candidate extracting step, on the auxiliary wave which is obtained in the auxiliary wave producing step, and selecting a cycle of a rhythm cycle candidate wave which has a peak in the auxiliary wave, as a true cycle.

According to the configuration, the cycle of a repetitive rhythmic motion can be accurately measured. Therefore, information on a body motion of a patient of Parkinson's disease or the like can be measured, recorded, and stored not only in an examination by a doctor in an outpatient visit, a round in the hospital, or the like, but also in a continuous manner on a daily basis.

According to the configuration, furthermore, the pathological condition of a patient of Parkinson's disease or the like can be correctly known, and the severity or change of the pathological condition of an illness or disease such as Parkinson's disease can be finely evaluated. Based on the evaluation, moreover, treatment such as medical treatment can be given at an adequate timing. Therefore, this leads to improvement of healing and control of the disease, and QOL of the patient.

BRIEF DESCRIPTION OF THE DRAWINGS

In the accompanying drawings:

FIG. 3 illustrates an example of a process of pattern matching in the invention;

FIGS. 5A and 5B are graphs showing an example of extraction of candidates for a rhythm cycle by a step of extracting cycle candidates in the invention;

FIGS. 7A and 7B are graphs illustrating an example of a method of deciding a scale in the invention;

FIG. 12 is a graph showing an example of anisotropy;

FIGS. 17A and 17B are graphs in which peak positions of a gait rhythm are selected in Embodiment 1 of the invention;

FIGS. 18A and 18B are graphs in which peak positions of a gait rhythm are selected in Comparative example 1 of the invention;

FIGS. 20A and 20B are graphs in which peak positions of a gait rhythm are selected in Comparative example 2 of the invention;

FIGS. 21A and 21B are graphs showing a correlation between a gait cycle and an acceleration in Embodiment 3 of the invention;

FIGS. 23A and 23B are graphs in which peak positions of a gait rhythm are selected in Embodiment 5 of the invention; and FIGS. 24A and 24B are graphs in which peak positions of a gait rhythm are selected in Embodiment 5 of the invention.

DETAILED DESCRIPTION OF THE EXEMPLARY EMBODIMENTS

The apparatuses, systems, methods, and the like which are exemplified in the following description are one examples (typical examples) of embodiments of the invention, and the invention is not particularly limited to their contents as far as not departing the spirit of the invention.

An information processing method for a body motion signal as an embodiment of the invention, which is suitably used in evaluation of Parkinson's disease or the like (hereinafter, sometimes referred to simply as "present measuring method") is characterized in which the cycle of a repetitive rhythmic motion (hereinafter, sometimes referred to simply as simply as "rhythm cycle") is accurately measured based on body motion signal information.

The present measuring method corresponds to a method in an information processing apparatus for performing information processing on a body motion signal which is obtained by an operation in which a subject carries a body motion signal detecting apparatus having a body motion signal detection section that measures non-invasively and continuously at least a repetitive rhythmic motion of a human body and for extracting a result obtained in the information processing, the information processing including following steps of (1) to (3):

(1) a cycle candidate extracting step of applying a pattern matching process on the body motion signal information, and extracting a rhythm cycle candidate wave as rhythm cycle candidates related to the rhythmic motion;

(2) an auxiliary-wave producing step of performing −1 or more times integration on the body motion signal information to obtain a motion trajectory, and performing coarse-graining on the motion trajectory to produce an auxiliary wave; and (3) a cycle selecting step of superimposing the rhythm cycle candidate wave which is extracted in the cycle candidate extracting step, on the auxiliary wave which is obtained in the auxiliary wave producing step, and selecting a cycle of a rhythm cycle candidate wave which has a peak in the auxiliary wave, as a true cycle.

According to the present measuring method, the cycle of the repetitive rhythmic motion can be accurately measured.

Therefore, it is possible to monitor also the situation of the daily life of the subject. For example, the subject or patient oneself or the doctor can correctly determine the severity or change of the pathological condition of an illness or disease such as Parkinson's disease, from the body motion signal (hereinafter, sometimes referred to as "body motion signal information") which is obtained by a body motion detecting apparatus, or information which is obtained by performing information processing on the body motion signal.

Figure 1:
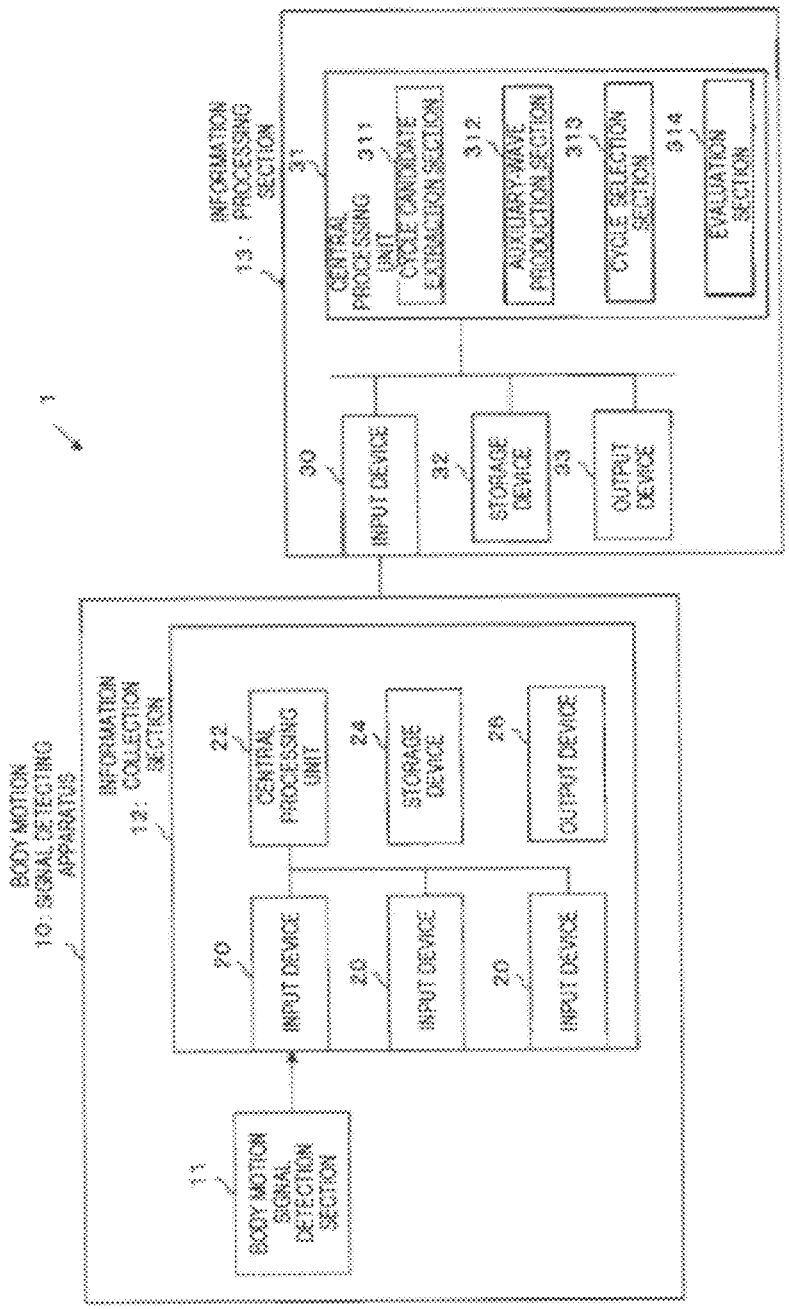
FIG. 1 is a block diagram showing an example of the configuration of a system of the invention.

FIG. 1 shows the configuration of an information processing system (hereinafter, sometimes referred to simply as "present system") for the body motion signal which is an example of the embodiment. The present system 1 includes, for example, a body motion signal detecting apparatus 10 and an information processing section (information processing apparatus) 13.

Figure 2:
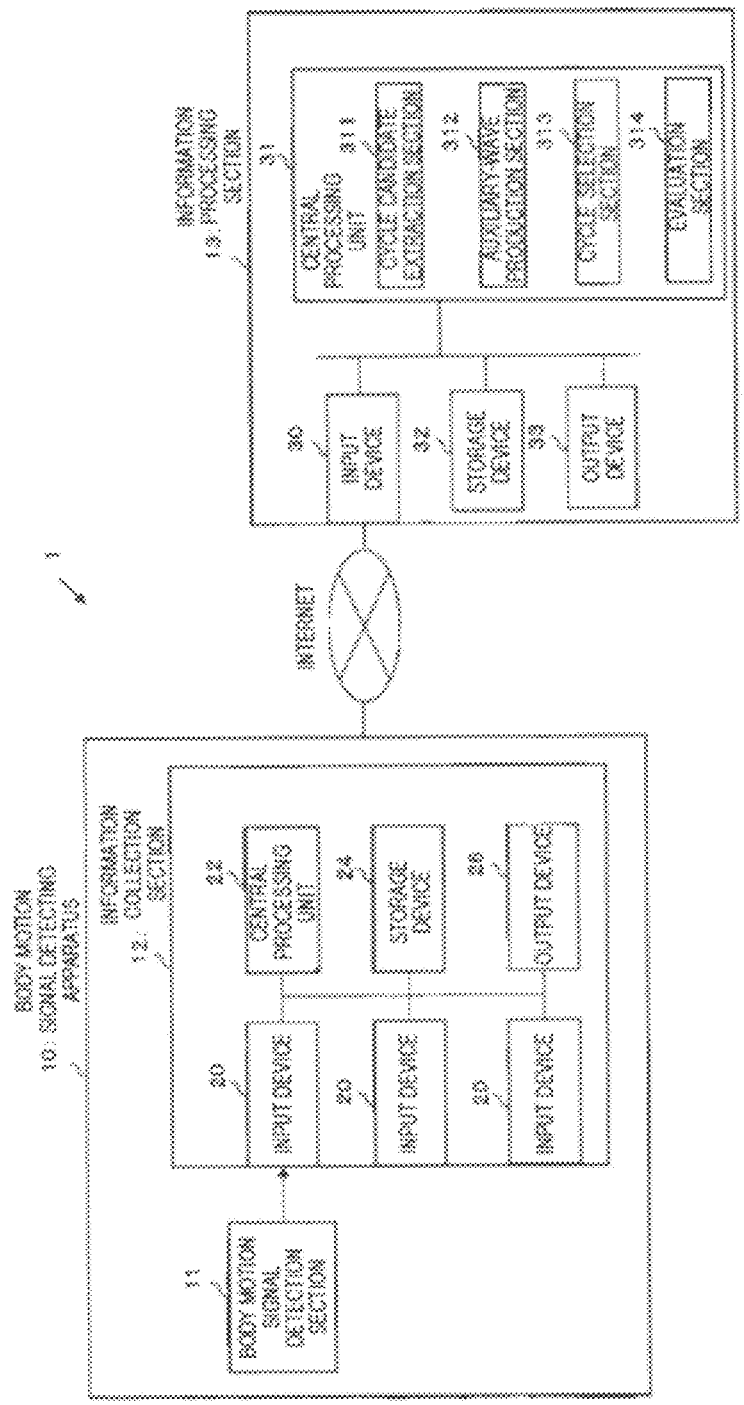
FIG. 2 is a block diagram showing an example of the configuration of the system of the invention.

The body motion signal detecting apparatus 10 and the information processing section 13 are communicably connected to each other. As shown in FIG. 2, the body motion signal detecting apparatus 10 and the information processing section 13 may be connected to each other through the Internet.

Alternatively, the body motion signal detecting apparatus 10 and the information processing section 13 may be connected to each other through a wireless connection such as a wireless LAN (Local Area Network) and Bluetooth (registered trademark). Namely, the body motion signal detecting apparatus 10 and the information processing section 13 are communicably connected to each other through communicating means such as wireless communication or wired communication.

The body motion signal detecting apparatus 10 which is used in the present measuring method has at least a body motion signal detection section 11. The body motion signal detection section 11 is not particularly limited as far as it corresponds to means which, as body motion signal information, can measure non-invasively and continuously a repetitive rhythmic motion of the body such as a change of a force, a change of the spatial position of the body, a change of a wave and micro energy such as sound, electromagnetic wave, or the like emitted from the body, and a change of the field surrounding the body. Here, the term of non-invasively means, for example, that the body of the subject is not damaged, or that no burden is imposed on the subject.

As the time period when body motion signal information is measured by the body motion signal detection section 11, usually, a continuous time period of 1 hour or longer is preferable, 12 hours or longer is more preferable, and 24 hours or longer is further preferable. According to the configuration, information of a body motion of the subject including a patient of Parkinson's disease or the like can be measured, and the pathological condition can be accurately known.

The body motion signal information (hereinafter, sometimes referred to as "biological signal information") detected by the body motion signal detection section 11 is, for example, a repetitive rhythmic motion, i.e., a rhythm associated with a repetitive rhythmic motion caused by a voluntary movement of a human.

The repetitive rhythmic motion may be any kind of rhythm as far as a repetitive motion is conducted at a certain cycle. Specifically, for example, the rhythm may be the gait rhythm, the stepping rhythm, the clapping rhythm, the masticatory rhythm, the foot tapping rhythm, the rhythm of eye movement, the blinking rhythm, and the like. In the invention, it is particularly preferable to detect the gait rhythm. When the gait rhythm is detected, it is possible to correctly know the severity, change of the pathological condition, or the like of an illness or disease such as Parkinson's disease or the like.

A device which detects the body motion signal information is adequately selected in accordance with the kind of the signal to be detected. Examples are a small acceleration sensor, a speed sensor, and a position sensor. In the case where the gait rhythm is detected, usually, an acceleration sensor which measures the acceleration of a body motion is preferably used.

As an acceleration sensor, any of one- to three-axis ones may be arbitrarily used. A three-axis acceleration sensor which detects accelerations acting in three directions or the vertical, horizontal anteroposterior, and horizontal lateral directions in walking is preferably used.

The body motion signal detecting apparatus 10 which is used in the present measuring method may have an information collection section 12 which records the body motion signal obtained by the body motion signal detection section 11. As shown in FIGS. 1 and 2, usually, the body motion signal detection section 11 and the information collection section 12 are accommodated in the same housing (for example, the body motion signal detecting apparatus 10). Alternatively, for example, only the body motion signal detection section 11 may be independently provided depending on a detecting method.

Namely, for example, the body motion signal detecting apparatus 10 includes the body motion signal detection section 11, but may not include the information collection section 12. In this case, for example, a configuration where the information collection section 12 receives the body motion signal information detected by the body motion signal detection section 11 through a wired connection such as the Internet, or a wireless connection such as a wireless LAN or Bluetooth, and stores the information may be employed.

In this case, the body motion signal detecting apparatus 10 has a function of transmitting the body motion signal information detected by the body motion signal detection section 11 to the information collection section 12 through wireless or wired connection. In the case where the body motion signal detection section 11 and the information collection section 12 are accommodated in the same housing irrespective of whether the information processing section 13 is detachable or not, for example, the body motion signal detecting apparatus 10 has a function of transmitting the body motion signal information recorded in the information collection section 12 to the information processing section 13.

More specifically, the body motion signal detecting apparatus 10 has a function of transmitting the body motion signal information to an input device 30 (described later) of the information processing section 13 through wireless or wired communicating means. These functions are realized by various well-known techniques. For example, they are realized by a central processing unit, not shown in figures, which is included in the body motion signal detecting apparatus 10 and by executing programs stored in storage devices inside or outside the body motion signal detecting apparatus 10.

For example, the body motion signal detecting apparatus 10 is configured so as to be portable. The position where the body motion signal detecting apparatus 10 is attached to the subject is not particularly limited as far as it is in a position where a body motion can be detected, and the body motion signal detecting apparatus 10 can be attached without giving a sense of discomfort to the subject. From the viewpoint of portability, the body motion signal detecting apparatus 10 is preferably attached so as to be mounted, connected, or housed to an article which the subject habitually wears, such as eyeglasses, a hat, clothes, a shoe, a belt, a watch, a bag, an accessory, a portable terminal, or a portable audio device.

In the case, for example, where the acceleration sensor is used as the body motion signal detection section 11 and the gait rhythm of the subject is obtained as the body motion signal information, the apparatus is preferably attached to the vicinity of the lumbar of the subject.

From the viewpoint of continuous measurement, the body motion signal detecting apparatus 10 is preferably always attached to the body. Alternatively, a configuration may be employed where, in the case where the attachment may disturb the convenience of the life of the subject, and in the time period when the occurrence rate of a body motion of the subject, particularly a repetitive rhythmic motion is low, such as while bathing and sleeping, the body motion signal detecting apparatus 10 is temporarily detached.

In the case where the body motion signal detecting apparatus 10 has the information collection section 12, the body motion signal information obtained from the body motion signal detection section 11 is recorded and stored in the information collection section 12. As shown in FIG. 1, for example, the information collection section 12 may include input devices 20 to which the signal from the body motion signal detection section 11 is input, a central processing unit 22 which is connected to the input devices 20, a storage device 24, an output device 26, and the like. However, the configuration is not limited to this, and may be arbitrarily changed.

In the example shown in FIG. 1, the information collection section 12 includes the three input devices 20. Alternatively, the information collection section 12 may include one or two input devices 20, or four or more input devices 20. For example, the information collection section 12 may not include the central processing unit 22. Moreover, for example, the information collection section 12 may not include the output device 26.

The information collection section 12 may be non-detachably accommodated in the body motion signal detecting apparatus 10. Alternatively, for example, the information collection section 12 may be configured by a detachable device, for example, a removable medium such as a memory card. Namely, the information collection section 12 is disposed so as to be detachable with respect to the body motion signal detecting apparatus 10, and records the body motion signal information.

The storage device 24 is a storage device which can store various kinds of information, such as a RAM (Random Access Memory), an HDD (Hard Disk Drive), an SSD (Solid State Drive), or a flash memory. Specifically, for example, the storage device 24 stores the body motion signal information obtained from the body motion signal detecting apparatus 10.

The input devices 20 are interfaces which are communicably connected to the body motion signal detection section 11. The input devices 20 temporarily store the body motion signal information which is sent, for example, from the body motion signal detecting apparatus 10.

The central processing unit 22 is a processing unit which executes various programs stored, for example, in the storage device 24 to perform various calculations and controls, thereby realizing various functions.

The output device 26 outputs an analysis result obtained in the body motion signal detection section 11, and is a monitoring device or the like.

In the present measuring method, the body motion signal information obtained by the body motion signal detection section 11 is analyzed by the information processing section 13. The information processing section 13 may be accommodated in the same housing (for example, the body motion signal detecting apparatus 10) as the body motion signal detection section 11 or the information collection section 12, or incorporated in, for example, an external computer which is different from the housing. The information processing section 13 may be configured, for example, so that programs for performing processes which will be described later are incorporated therein.

In the present measuring method, although illustration is omitted for the sake of convenience, the body motion signal detection section 11, the information collection section 12, the information processing section 13 may be formed separately from one another. In this case, data exchange between the body motion signal detection section 11, the information collection section 12, and the information processing section 13 may be performed through wired or wireless connection, and data which are recorded and stored in the information collection section 12 may be exchanged to and from the information processing section 13 through various recording media and the like.

The information collection section 12 may be contained in the body motion signal detecting apparatus 10, but detachably formed, and the information collection section 12 may be connected to the computer in which the information processing section 13 is accommodated. In this case, data exchange can be performed even when the body motion signal detecting apparatus 10 and the information processing section 13 are connected to each other through communicating means such as wired communication or wireless communication.

Hereinafter, the same shall apply with respect to that, in the case where the information collection section 12 is detachable with respect to the body motion signal detecting apparatus 10, data exchange can be performed even when the body motion signal detecting apparatus 10 and the information processing section 13 are not connected to each other through communicating means such as wired communication or wireless communication.

Also a configuration where a result extracted by the information processing section 13 is sent to the body motion signal detecting apparatus 10 by a well-known method is preferable. Moreover, also a configuration where the result is sent to the doctor in charge is preferable. Any method may be employed as the sending method. Specifically, for example, a method in which the result is sent in the form of electronic data to a terminal connected to the computer that is the information processing section 13, through wired or wireless connection is preferable.

For example, the information processing section 13 may be a PC (Personal Computer) or the like, and include the input device 30, a central processing unit 31, a storage device 32, and an output device 33. However, the configuration is not limited to this, and may be arbitrarily changed. Preferably, the input device 30, the central processing unit 31, the storage device 32, and the output device 33 are communicably connected to one another.

The input device 30 is an interface which is communicably connected, for example, to the body motion signal detecting apparatus 10 or the information collection section 12 through communicating means such as wired communication or wireless communication. When the information collection section 12 which is detached from the body motion signal detecting apparatus 10 and delivered is connected to the input device 30, for example, the body motion signal information recorded in the information collection section 12 is imported into the information processing section 13. In this case, the central processing unit 31 reads the body motion signal information recorded in the information collection section 12, and performs various processes.

In the case where the body motion signal information recorded in the information collection section 12 is transmitted (transferred) from the body motion signal detecting apparatus 10 through communicating means such as wired communication or wireless communication, for example, the transferred body motion signal information is input to the input device 30 to be imported into the information processing section 13. In this case, the central processing unit 31 performs various processes by using the body motion signal information which is input to the input device 30. Namely, the input device 30 functions as an information import section which imports the body motion signal information.

The storage device 32 is a storage device which can store various kinds of information, such as a RAM, a ROM (Read Only Memory), an HDD, an SSD, or a flash memory.

The output device 33 includes, for example, a display section which outputs various process results obtained in the central processing unit 31, and is a monitoring device or the like. For example, the output device 33 may be disposed separately from the information processing section 13.

The central processing unit 31 is a processing unit which executes various programs stored in, for example, the storage device 32 to perform various calculations and controls, thereby realizing various functions.

For example, the central processing unit 31 executes programs stored in the storage device 32 to function as a cycle candidate extraction section 311, an auxiliary-wave production section 312, a cycle selection section 313, and an evaluation section 314.

Namely, the programs are programs which cause the central processing unit 31 to execute, for example, the cycle candidate extracting step which is executed by the cycle candidate extraction section 311 that will be described later, the auxiliary-wave producing step which is executed by the auxiliary-wave production section 312, the cycle selecting step which is executed by the cycle selection section 313, and an evaluating step which is executed by the evaluation section 314.

The cycle candidate extraction section 311 performs pattern matching (the autocorrelation method or the like) by using the body motion signal information imported by, for example, the input device 30, thereby extracting candidates for the rhythm cycle. Namely, the cycle candidate extraction section 311 functions as a cycle candidate extraction section which applies a pattern matching process on the body motion signal information, to extract a rhythm cycle candidate wave as rhythm cycle candidates related to a rhythmic motion.

While using the body motion signal information imported by, for example, the input device 30, the auxiliary-wave production section 312 performs −1 or more times integration on the body motion signal information to obtain a motion trajectory, and performs coarse-graining on the motion trajectory, thereby producing an auxiliary wave for determining a true rhythm cycle (accurate rhythm cycle). Namely, the auxiliary-wave production section 312 functions as an auxiliary-wave production section which performs −1 or more times integration on the body motion signal information to obtain a motion trajectory, and which performs coarse-graining on the motion trajectory to produce the auxiliary wave.

For example, the cycle selection section 313 superimposes the rhythm cycle candidate wave which is extracted by the cycle candidate extraction section 311, on the auxiliary wave which is produced by the auxiliary-wave production section 312, and selects one peak interval in each region surrounded by the auxiliary wave, as a true rhythm cycle.

For example, the cycle selection section 313 selects the interval of the maximum peak in the region surrounded by the auxiliary wave, as a true rhythm cycle. In other words, the cycle selection section 313 selects the cycle of the rhythm cycle candidate wave which has the maximum peak in each region surrounded by the auxiliary wave, as a true rhythm cycle.

Namely, the cycle selection section 313 functions as a cycle selection section which superimposes the rhythm cycle candidate wave that is extracted by the cycle candidate extraction section, on the auxiliary wave that is obtained in the auxiliary-wave production section, and which selects the cycle of a rhythm cycle candidate wave having a peak in the auxiliary wave, as a true cycle (hereinafter, sometimes referred to as "true rhythm cycle").

The evaluation section 314 performs a process of evaluating Parkinson's disease based on the true rhythm cycle selected by, for example, the cycle selection section 313. For example, the evaluation section 314 evaluates the severity of Parkinson's disease based on the true rhythm cycle selected by the cycle selection section 313.

One mode of the present measuring method will be described with reference to FIG. 1. First, the body motion signal detection section 11 carried by the subject detects continuous body motion signal information of the subject, and the body motion signal information is sent to the information collection section 12 to be recorded and stored therein. The information processing section 13 reads out and analyzes the body motion signal information.

A result which is extracted by the analysis is output to an adequate output device such as the output device 33 and the output device 26. In the case where the extracted result is output to the output device 26, the extracted result is transmitted from the information processing section 13 to the body motion signal detecting apparatus 10, and then output from the output device 26.

The analysis and evaluation of the body motion signal information in the information processing section 13 may be performed in real time with the measurement or recording and storing of the body motion signal information. Alternatively, for example, the body motion signal information may be measured for a constant time period, recorded, and stored, and then analysis and evaluation may be performed.

For example, a mode where the body motion signal information is evaluated in real time and notified to the patient (subject) may be employed. In this case, when the disease of the patient become worse, the patient can receive the notification and perform an adequate action such as taking of a medicine or going to the hospital.

Furthermore, for example, a mode where the body motion signal information is stored for a constant time period, then evaluated, and, when the patient goes to the hospital, a result of the evaluation is notified to the doctor in charge may be employed. In this case, the doctor can quantitatively know the diurnal variation of the disease, the efficacy of a medicine, and the like, on the spot, and easily decide an exact future course of treatment.

In the present measuring method, the information processing section 13 performs data analysis on the body motion signal information recorded in the information collection section 12, and extracts information for evaluating the state of Parkinson's disease, or specifically for example the severity or change of Parkinson's disease.

For example, the information processing section 13 may include the input device 30, the central processing unit 31 connected to the input device, the storage device 32, the output device 33, etc. However, the configuration is not limited to this, and may be adequately changed.

In the thus configured information processing section 13, for example, data which are input from the information collection section 12, those stored in the storage device 32 in the information processing section 13, and the like can be read, and the central processing unit 31 can perform the following process.

The information processing section 13 performs information processing including the following steps. First, the cycle candidate extraction section 311 reads the body motion signal recorded by the information collection section 12, and performs pattern matching (the autocorrelation method or the like), thereby extracting candidates for the rhythm cycle (the cycle candidate extracting step).

In the pattern matching, a pattern matching method or template matching method which is known and usually used can be used. Specifically, for example, the method described in GAZO SHORI KOGAKU (SUEMATSU Ryoichi and YAMADA Hironao, KORONA SHA) and the like is used.

In the case where three-axis acceleration signals are obtained as the body motion signal, first, the cycle candidate extraction section 311 selects an adequate reference wave from the signals, and performs matching with original data. The reference wave means data of a certain constant width in the body motion signal, and any signal may be selected as the reference wave.

In a repetitive rhythmic motion such as gait, for example, an acceleration signal is formed by a waveform having a peak. However, it is not always necessary to select a signal of a constant time period centered on the peak, as the reference wave. The reference wave may be selected while the center position is deviated from the peak time.

However, it is preferable that pattern matching is performed while the center position of the reference wave is randomly selected, and the reference wave is selected with setting a position where the sum of the intensities of rhythm cycle candidates is maximum, as the optimum center position. With respect to the width of the reference wave, in a time scale S which is determined by a scale decision process that will be described later, preferably, S/2 is used as the optimum width.

Specifically, for example, the coordinates of the reference wave is set as Exp. (i), and three-dimensional autocorrelation coefficients are calculated by following Exp. (ii) (FIG. 3).

[Exp. 1]

$$(x(1),y(1),z(1)),(x(2),y(2),z(2)), \ldots (x(p),y(p),z(p)) \quad \text{(i)}$$

In the above, the averages of the p numbers of x, y, and z are assumed to be zero.

[Exp. 2]

$$\frac{\dfrac{1}{p}\sum_{i=1}^{p}[x(i)x(i+T)+y(i)y(i+T)+z(i)+z(i+T)]}{\left\{\dfrac{1}{p}\sum_{i=1}^{p}[x(i)^2+y(i)^2+z(i)^2]\right\}^{\frac{1}{2}}\left\{\dfrac{1}{p}\sum_{i=1}^{p}[x(i+T)+y(i+T)^2+z(i+T)^2]\right\}} \quad \text{(ii)}$$

The above autocorrelation coefficients are so-called scalar quantities, and are not dependent on the manner of setting the coordinate system. Namely, this is preferable from the viewpoint that the same values are obtained even when, during a body motion measurement, a device causes rotational displacement in an attachment portion (for example, a belt, a pocket, or a bag).

Figures 4A, 4B:
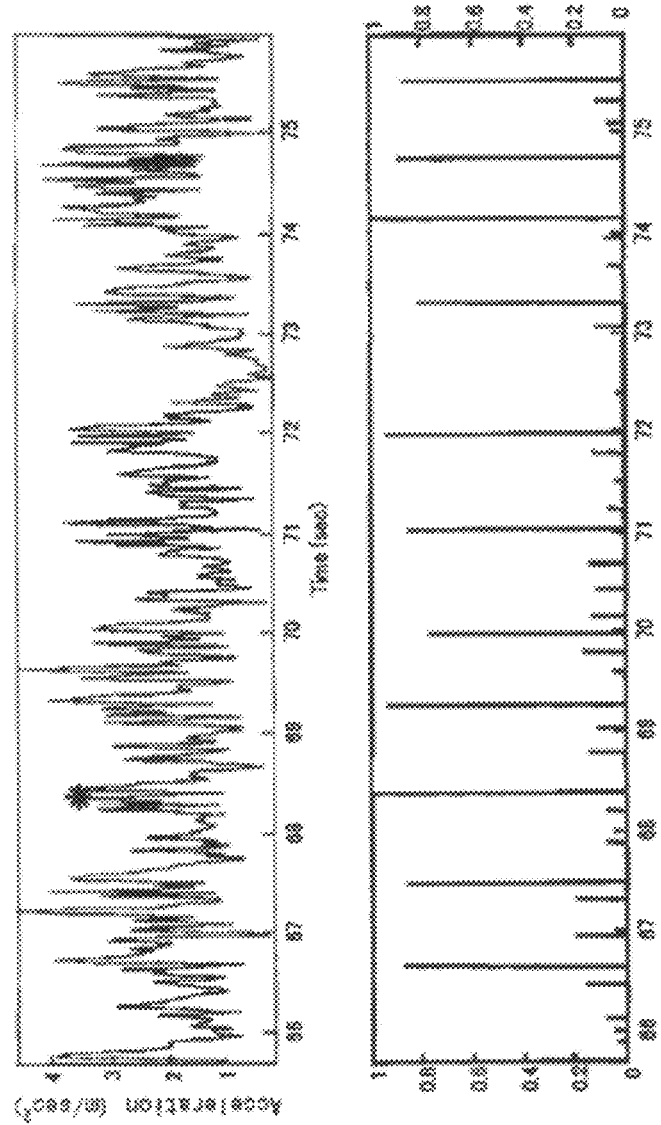
FIGS. 4A and 4B are graphs showing an example of extraction of candidates for a rhythm cycle by a pattern matching in the invention.

With reference to FIG. 4, the pattern matching will be described. FIG. 4A shows a waveform in which three-dimensional acceleration data recorded by a body motion information collection section are converted into absolute values by following Exp. (iii).

[Exp. 3]

$$r = \sqrt{x^2 + y^2 + z^2} \quad \text{(iii)}$$

FIG. 4B shows a result of an operation in which, in the acceleration wave, a region having a width of 0.5 sec. centered on the symbol of * in FIG. 4A is selected as the reference wave, pattern matching is performed based on the above expression, and rhythm cycle candidates are obtained. FIG. 5B shows the case where selection is performed while the peak position of the reference wave is deviated from a peak of an actual acceleration signal (the symbol of * in FIG. 5A). Also in this case, rhythm cycle candidates can be similarly extracted [FIG. 5B].

Next, the auxiliary-wave production section 312 reads the body motion signal recorded in the information collection section 12, and performs −1 or more times integration on the body motion signal to obtain a motion trajectory. Preferably, the integration number is −1 or more and 5 or less. Namely, the integration number is preferably −1, 0, 1, 2, 3, 4, and 5, and more preferably 2 to 3. Here, integration of −1 time means first differential.

Figures 6A, 6B:
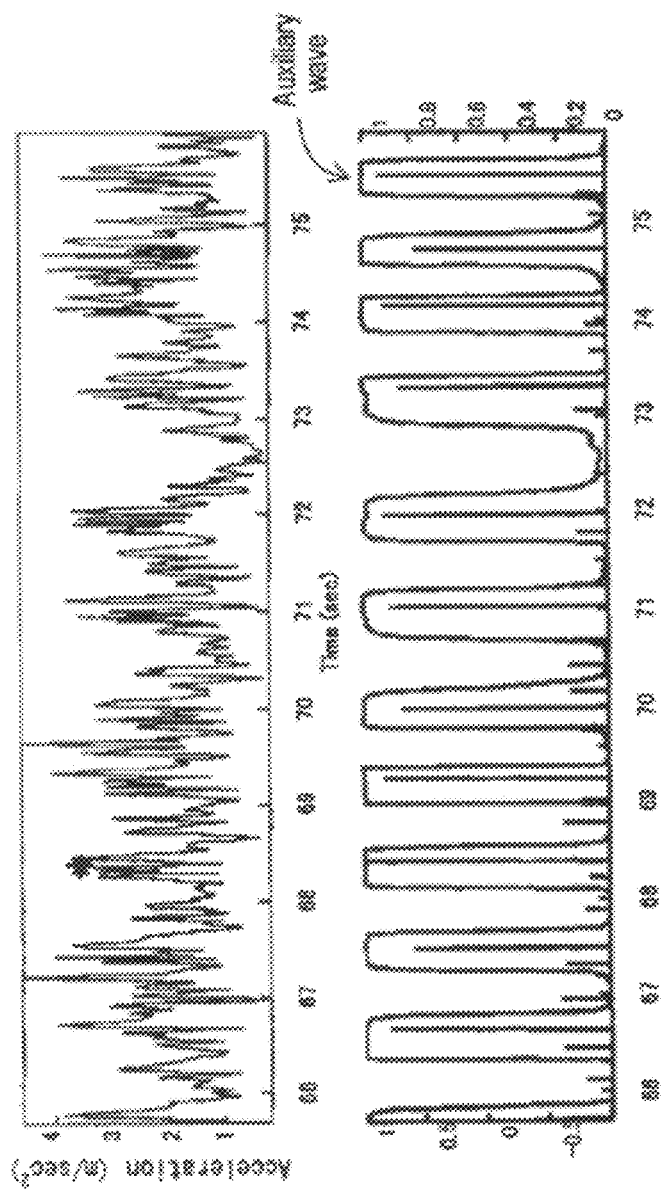
FIGS. 6A and 6B are graphs showing an example of production of an auxiliary wave by a step of producing an auxiliary wave in the invention.

The auxiliary-wave production section 312 performs coarse-graining on the obtained motion trajectory to produce the auxiliary wave for determining a true rhythm cycle [the auxiliary-wave producing step: see FIG. 6B]. In FIG. 6B, the wide waveform similar to a rectangular wave is the auxiliary wave, and FIG. 6A is similar to FIG. 4A. The auxiliary wave is obtained by deciding the time scale S from the motion trajectory which is obtained in the above, and performing coarse-graining on the motion trajectory by using the scale.

Here, the temporal and spatial sizes related to a main cyclic motion shown by the trajectory are referred to as the scale. When the scale is used, the pattern matching and the coarse-graining of the motion trajectory can be efficiently performed. Specifically, the scale can be decided in the following manner.

The auxiliary-wave production section 312 sets an appropriate time region T (here, 2 sec.) by using the motion trajectory which is obtained by twice integrating the acceleration, and obtains the scale in the time period. The time region T may be set to any value as far as it is equal to or longer than the objective rhythm cycle. In the case of the gait rhythm, for example, the cycle is usually about 1 sec., and hence it is sufficient that the time region T is equal to or longer than the time period. In order to eliminate an error due to previous assumption of the cycle, however, it is preferable to set the time region to be 2 sec. or longer.

First, the auxiliary-wave production section 312 finely changes the duration t between 0 to T, and obtains an average value D(t) of the distance between two points on the trajectory which are separated from each other by the duration. When the duration is indicated by t, the measurement time interval of the acceleration data is indicated by dt, and an integer satisfying t+Ndt≤T<t+(N+1)dt, specifically, the distance between two points at time 0 and time t, that between two points at time dt and time t+dt, and that between two points at time 2dt and time t+2dt, i.e., an (N+1) number of distances between two points at time ndt and time t+ndt (n=0, 1, ..., N) are obtained, and the average of the obtained (N+1) number of distances is indicated by D(t).

Next, the auxiliary-wave production section 312 obtains the maximum value MAXD(t) of D(t) with respect to the zone of times 0 to t [the solid line graphs in FIGS. 7A and 7B]. Specifically, the auxiliary-wave production section 312 obtains the maximum value of D(t0) when the time t0 is changed between 0≤t0≤t, and sets the maximum value as MAXD(t). Finally, the auxiliary-wave production section 312 calculates MAXD(t)−D(t) [the broken line graphs in FIGS. 7A and 7B].

Figure 8:
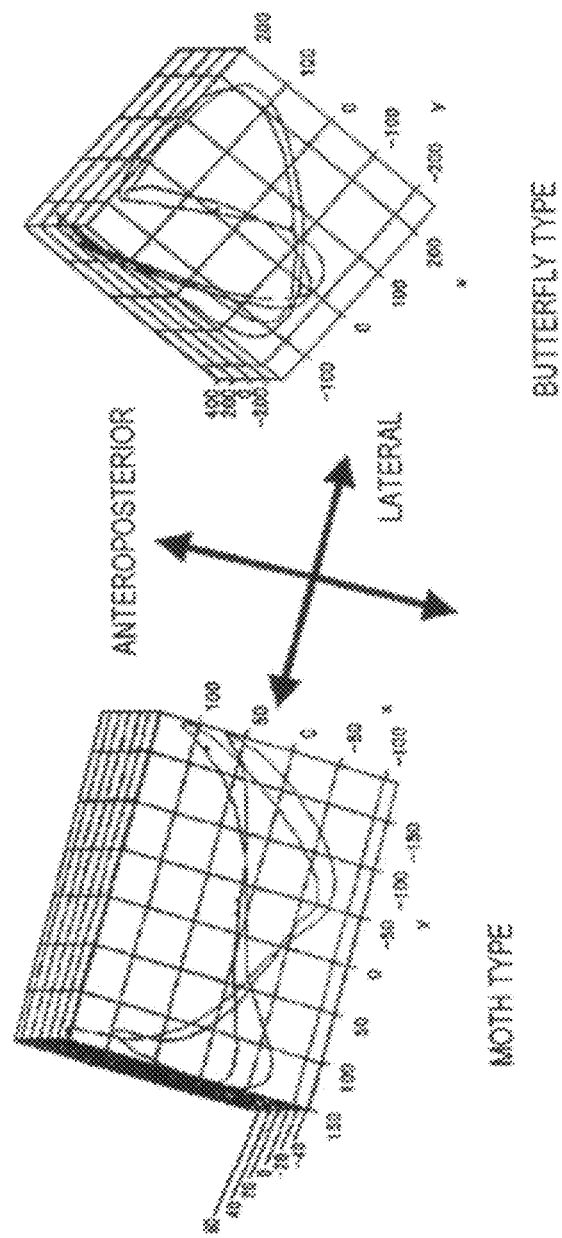
FIG. 8 is a view showing an example of a pattern of a gait trajectory.

As the body motion signal, for example, the gait trajectory is roughly classified into the following two patterns (FIG. 8). First, a trajectory in which the variation width in the lateral direction is larger than that in the anteroposterior direction, and which is similar to a shape where wings are spread is called "moth" type, and that having a contrasting shape where wings are closed is called "butterfly" type.

The discrimination between the two types is performed automatically and accurately by the auxiliary-wave production section 312 while the following information is quantified. In the case of the moth type, the principal axis [the broken line in FIG. 9A] which is obtained by analyzing main components of the trajectory extends in a direction passing direction the two wings, and hence the rotational symmetry around the axis is low [see FIG. 9A]. In the case of the butterfly type, on the contrary, the principal axis [the broken line in FIG. 10A] is parallel to the planes of the wings, and hence the rotational symmetry is high [see FIG. 10A].

Figure 9B:
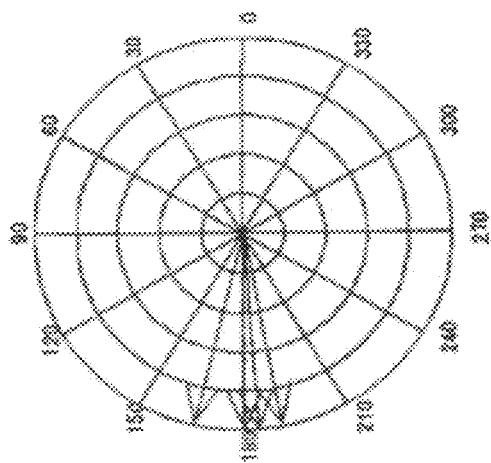
FIGS. 9A and 9B illustrate an example of a method of determining a gait type in the invention.

For example, the auxiliary-wave production section 312 produces a plane which is perpendicular to the principal axis, plots the trajectory which intersects the plane on the plane, and, when the points are concentrated into an angular range of 180 degrees as viewed from the origin, determines that the trajectory is of the moth type [FIG. 9B].

Figure 9A:
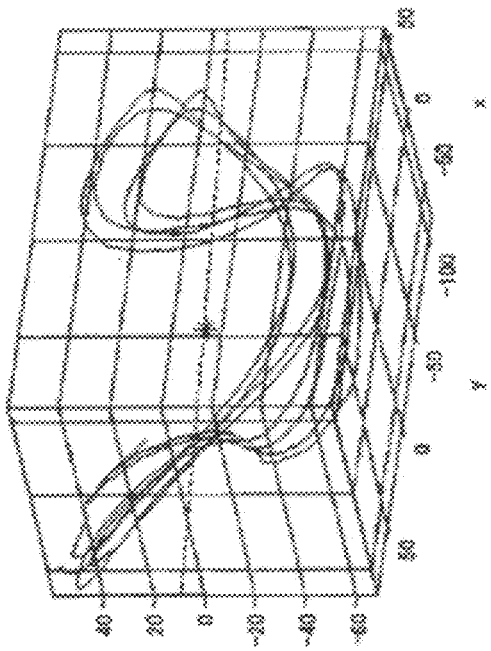
Figure 10A:
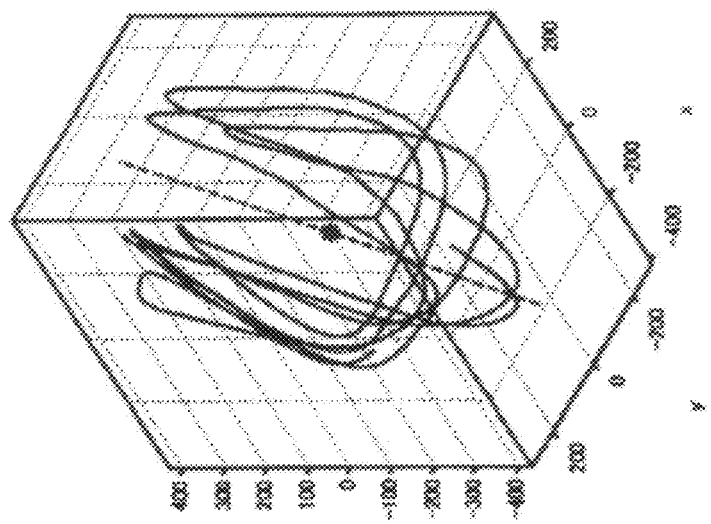
FIGS. 10A and 10B illustrate an example of a method of determining a gait type in the invention.

More specifically, for example, the auxiliary-wave production section 312 produces a plane which is perpendicular to the principal axis, and which passes through the origin [the symbols of * in FIGS. 9A and 10A], plots points (hereinafter, sometimes referred to as points of intersection] where the trajectory intersects the plane, on the plane, and, when all the points of intersection exist in an angular range of 180 degrees as viewed from the origin, determines that the trajectory is of the moth type [FIG. 9B].

In the example shown in FIG. 9B, the directions of the points of intersection as viewed from the origin are indicated by the arrows. In the example shown in FIG. 9B, it is seen that all the arrows are concentrated in a region from about 150 degrees to 210 degrees, i.e., a range of 60 degrees. Namely, all the points of intersection exist in the angular range of 180 degrees as viewed from the origin, and hence the auxiliary-wave production section 312 can determine that the gait trajectory is of the moth type.

Figure 10B:
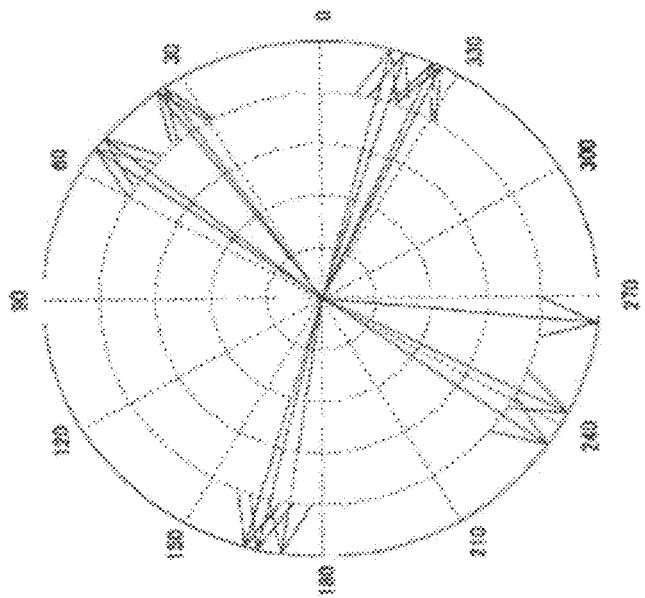

In the case of the butterfly type, by contrast, points of intersection are not localized within an angular range of 180 degrees as viewed from the origin [FIG. 10B]. Namely, all the points of intersection do not exist in the angular range of 180 degrees as viewed from the origin, and hence the auxiliary-wave production section 312 can determine that the gait trajectory is of the butterfly type.

With respect to the butterfly type, the auxiliary-wave production section 312 obtains a quadruple of the initial time period [* in FIG. 7A, here 0.23 sec.] when MAXD(t) is constant, as the time scale. It coincides with the peak position (○ in FIG. 7A, here 0.93 sec.) of MAXD(t)−D(t). The time scale corresponds also to the average gait cycle in the time region T. The value [470 in FIG. 7A, the unit is 0.1 mm] of MAXD(t) which is constant is the spatial scale.

With respect to the moth type, a gradual change occurs until MAXD(t) becomes constant [FIG. 7B]. Therefore, the auxiliary-wave production section 312 sets the peak position [in FIG. 7B, 0.98 sec.] of MAXD(t)−D(t) as the time scale.

Figure 11A:
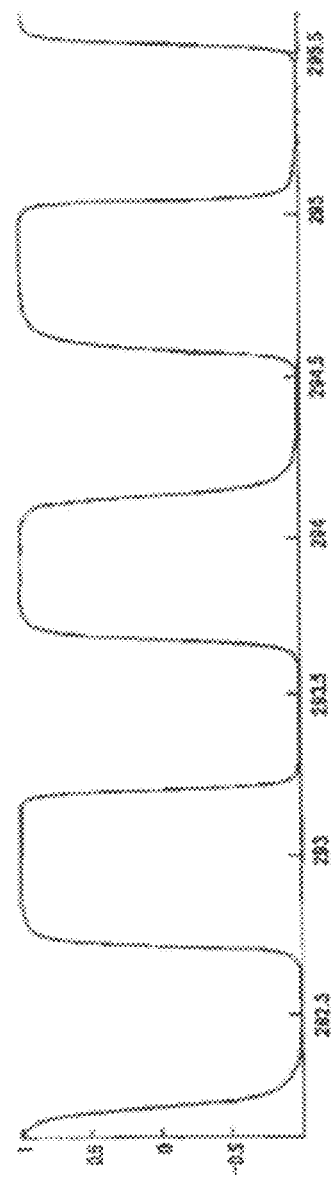
FIGS. 11A and 11B are graphs showing an example of production of an auxiliary wave by a step of producing an auxiliary wave in the invention.
Figure 11B:
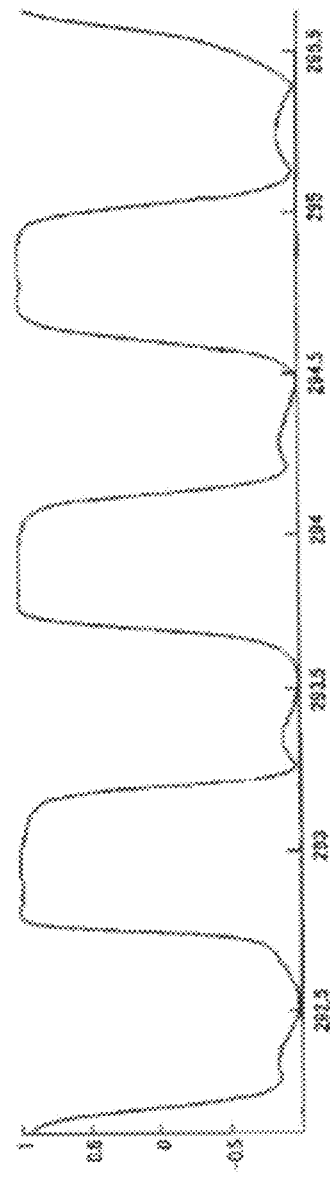

In the case of the moth type, however, it is not always necessary to set in detail the time scale when the auxiliary wave is to be produced. For example, FIGS. 11A and 11B show auxiliary waves in the case where 1 and 0.6 sec. are set as the time scale, respectively. The both waves are a clear rectangular wave. Practically, there arises no problem even when any one of the auxiliary waves is used.

In order cope with the case where the gait pace is suddenly changed, preferably, such a scale is finely obtained, for example, at intervals of 1 sec.

In the method of performing coarse-graining on the motion trajectory on the above-described scale, coarse-graining is a physical term meaning that a thing is coarsely viewed, and realized by a method such as averaging, integrating, or determining a representative value of data which are finely measured, at constant intervals.

Specifically, for example, the auxiliary-wave production section 312 can produce the auxiliary wave by obtaining following vector time-series (Exp. (v)) as coarse-graining from trajectory coordinate time-series (Exp. (iv)), and, with respect to the data, calculating an inner product of a reference point vector (=the reference wave having zero width) and a vector at another time.

[Exp. 4]

$$(x(t), y(t), z(t)) \quad \text{(iv)}$$

[Exp. 5]

$$\left( x\left(t+\frac{S}{4}\right) - x\left(t-\frac{S}{4}\right), y\left(t+\frac{S}{4}\right) - y\left(t-\frac{S}{4}\right), z\left(t+\frac{S}{4}\right) - z\left(t-\frac{S}{4}\right) \right) \quad \text{(v)}$$

In the example of the embodiment, the auxiliary wave is produced as described above, but the method is not limited to this. Another example of the method of producing the auxiliary wave will be described. The method is preferably used in the case where the auxiliary-wave production section 312 performs −1- or 1-time integration on the body motion signal information, thereby obtaining the motion trajectory.

The below-described auxiliary wave producing method can be applied commonly to the gait trajectories of the butterfly and moth types. First, the auxiliary-wave production section 312 performs −1 or 1 or more times integration on the body motion signal information imported by, for example, the input device 30, thereby obtaining the motion trajectory.

More specifically, in three-axis body motion signal information of the vertical, anteroposterior, and lateral directions, the body motion signal information of the lateral direction is subjected to −1 or 1 or more times integration, thereby obtaining the motion trajectory of the lateral direction.

Next, the auxiliary-wave production section 312 smoothes the motion trajectory in the lateral direction by using a low-pass filter having a time constant (filter time constant) A. Specifically, for example, a moving average filter of a duration (filter time constant) A is preferably used as the low-pass filter.

More preferably, a zero-phase moving average filter may be used as the low-pass filter. A zero-phase moving average filter means a moving average filter in which the phase shift is zero. A zero-phase moving average filter can be realized by using various known techniques, and its detail description is omitted.

The duration A is finely changed within a range which is equal to or shorter than a certain time period A0 ($0 \leq A \leq A0$). This A0 is set to a time period which is about a half of the objective rhythm cycle (for example, the rhythm cycle of gait). The appropriateness of the setting is determined by the method described later.

Next, with respect to the signal which is smoothed by the low-pass filter, the auxiliary-wave production section 312 calculates the anisotropy of the signal in a region of the duration A centered on a time a, i.e., a time region of a $-A/2 \leq a1 \leq a+A/2$.

The anisotropy is obtained by quantizing the degree at which a time-series signal is deviated toward a plus value or a minus value, and can be calculated by the following two methods, but not limited to these methods.

(1) When the average of data having a positive value in the data is indicated by P and the average of data having a negative value is indicated by M, the anisotropy=(P+M)/(P−M), and (2) when the number of data having a positive value in the data is indicated by P and that of data having a negative value is indicated by M, the anisotropy=(M−P)/(P+M).

FIG. 12 is a graph showing an example of a change of the anisotropy with respect to the time a. From the thus obtained time-series data of the anisotropy, the auxiliary-wave production section 312 extracts 2 adjacent points where the value of the anisotropy intersects the zero line in the direction from negative to positive (or from positive to negative) (● in FIG. 12).

With respect to the time interval between such two points, then, the auxiliary-wave production section 312 obtains an average value (scale) and its CV (standard deviation/average value: Coefficient of Variation). The CV and the scale are plotted while changing the filter time constant A, and the scale in the case where the CV has the minimum value is decided as a time scale B for coarse-graining.

Figure 13:
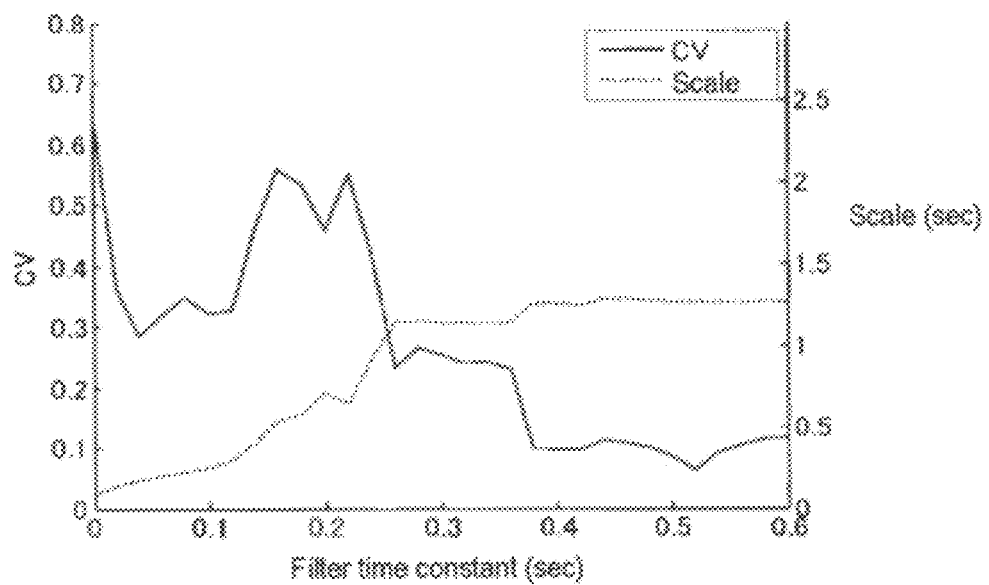
FIG. 13 is a graph showing an example of changes of dispersion and a scale with respect to a change of a time constant.

FIG. 13 is a graph showing an example of changes the CV and time scale B with respect to the filter time constant A. In the example of FIG. 13, when A=0.52 sec., the CV has the minimum value, and the scale at that time is 1.27 sec. This time scale B corresponds to the average gait cycle.

Here, the scale means an average time interval between times when an anisotropic wave (FIG. 12) intersects the zero line. In other words, therefore, the scale corresponds to the average cycle of the anisotropic waveform. Furthermore, the CV shows the dispersion of the time interval, i.e., the degree of regularity of the anisotropic waveform.

Therefore, the point where the CV is minimum corresponds to the case where the anisotropic waveform changes in the most regular (cyclic) manner. Namely, the anisotropic waveform in the case where the CV is minimum corresponds to main frequency components extracted from the original gait trajectory in the lateral direction. Therefore, the time scale B (i.e., the average cycle of the anisotropic waveform) at this time corresponds to the average cycle of the original gait trajectory.

In FIG. 13, A0=0.6 sec. is set. This is about a half of the rhythm cycle (time scale), and hence it can be determined that the setting of A0 is appropriate. On the contrary, when the obtained time scale is smaller than two times of A0, it is determined that the set value of A0 is excessively small, A0 is reset to a larger value, and then the above-described calculation is repeated.

Here, A0=0.6 sec. is equal to or shorter than a half of the obtained scale B (i.e., the average gait cycle) of 1.27 sec., and hence it is determined that the setting of A0 is appropriate. In the case where A0 is a half of the scale B, the setting of A0 is determined to be appropriate, because of the following reason.

For example, it is assumed that A0 is equivalent to the gait cycle. When the above-described low-pass filter process is performed by using such a time constant, the value of the waveform after the filter process is substantially zero, and there is no effect of the low-pass filter process. Therefore, $A(\leq A0)$ must be set to be shorter than the average gait cycle.

From the viewpoint of the calculation efficiency, A0 is set to be as short as possible. When A is about a half of the gait cycle, high-frequency components (components of a cycle which is a half of the cycle in the lateral direction) due to motions in the vertical and anteroposterior directions are eliminated by the filter process as described later, and hence the cycle in the lateral direction (=the gait cycle) can be accurately taken out.

Therefore, it is preferable that A0 is set to about a half of the average gait cycle, and the filter process is performed by using A the value of which is equal to or shorter than A0.

Hereinafter, a method in which a motion trajectory waveform X is smoothed by a low-pass filter having a time constant A1 to obtain an anisotropic wave Y at a duration A2 is abbreviated as Y=F(X, A1, A2). According to this notation, the above-described process can be expressed as Y=F(X, A, A).

Next, the auxiliary-wave production section 312 performs coarse-graining on the motion trajectory waveform X in the lateral direction by using Z=F(X, B/2, B1) where B indicates the obtained time scale, and produces an auxiliary wave Z based on an anisotropy evaluation. Here, B1 is a value which is equal to or smaller than B/2, and it is preferable that B1=B/4.

When it is unknown that which one of the three-axis acceleration signals (body motion signal information) is the signal in the lateral direction, the auxiliary-wave production section 312 performs the decision in the following manner.

Figure 14:
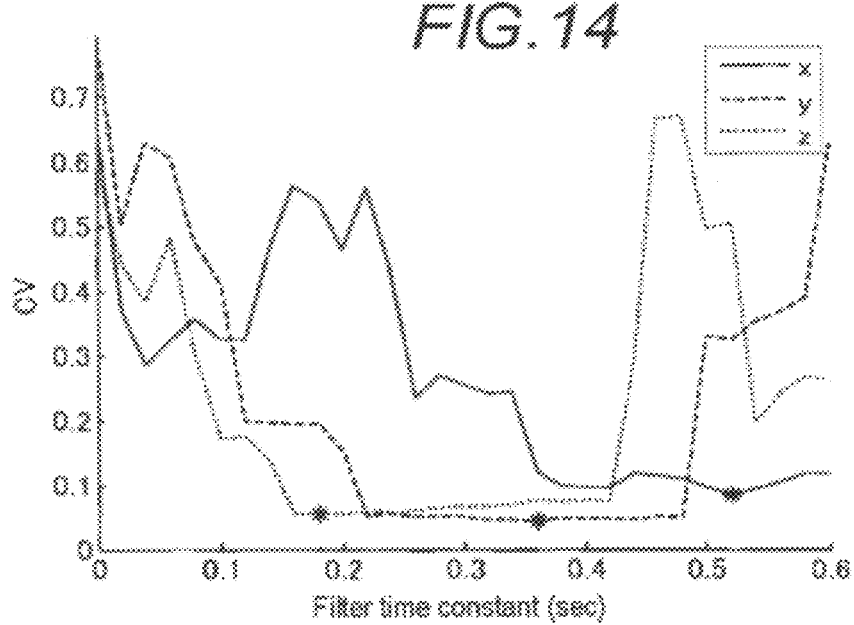
FIG. 14 is a graph showing an example of a change of dispersion with respect to a change of the time constant.

The auxiliary-wave production section 312 obtains the motion trajectories of all three axis directions, and, with respect to the motion trajectories in the three axis directions (x, y, z), obtains a relationship between the filter time constant A and the CV by using the above-described method. FIG. 14 is a graph showing an example of a change of the CV with respect to the filter time constant A. The minimum point is extracted from the motion trajectories in all three axis directions (* in FIG. 14). The signal in the lateral direction is a signal which provides the point of the largest filter time constant among these three points (the solid line in FIG. 14).

As described above, the anisotropic waveform in which the CV is minimum corresponds to a waveform which is obtained by smoothing the original gait trajectory by using a low-pass filter, and taking out a waveform of the strongest cyclicity. In order to obtain such an anisotropic waveform, it is required to use a filter in which, as the main cycle of the original gait trajectory is longer, the time constant is larger. In the gait rhythm, the cycle (gait cycle) in the lateral direction is about 1 sec., and the cycles in the vertical and anteroposterior directions are a half of the cycle.

In order that the anisotropic waveform of the strongest cyclicity is taken out by filtering of the gait trajectory in the lateral direction, therefore, it is necessary to use a time constant which is larger as compared to the vertical and anteroposterior directions. In the case where the characteristic is used in an opposite manner, it can be determined that the gait trajectory in the lateral direction provides the anisotropic waveform in which the optimum (the CV is minimum) time constant is longest.

In the case where the attaching position of the measuring apparatus is deviated and hence the three axis directions fail to completely coincide with the lateral, anteroposterior, and vertical directions, the auxiliary-wave production section 312 obtains a motion trajectory which extends along vectors emanating from the origin in all directions, produces a plot of the trajectory as shown in FIG. 14, and selects a vector in which the filter time constant of the minimum point is largest, as the lateral direction.

The auxiliary wave is a rectangular wave which varies in a substantially binary manner, and hence assists in uniquely determining the peak position without introducing no parameter such as a special threshold. When the auxiliary wave is obtained, the cycle selection section 313 superimposes it on the rhythm cycle candidate waves which are obtained in the cycle candidate extracting step, and selects, for example, the cycle of a rhythm cycle candidate wave which has the maximum peak in the region surrounded by the auxiliary wave, as a true rhythm cycle.

In the case where there are a plurality of peaks in the region surrounded by the auxiliary wave, the cycle selection section 313 may select the cycle of a rhythm cycle candidate wave which has the maximum peak or the cycle of a rhythm cycle candidate wave which has a peak other than the maximum peak, as a true rhythm cycle. This is because there is a possibility than even a rhythm cycle candidate wave which is obtained in the cycle candidate extracting step, and which do not have the maximum peak in the region surrounded by the auxiliary wave may be the rhythm cycle of the actual rhythmic motion.

When the cycle selection section 313 outputs the correctly obtained rhythm cycle to an adequate output device, for example, the thus correctly obtained rhythm cycle is output by the adequate output device. For example, the correctly obtained rhythm cycle is displayed on a display section disposed in the adequate output device (a displaying step).

For example, a calculation device disposed in the adequate output apparatus executes a predetermined program stored in a storage device disposed inside or outside the adequate output apparatus, whereby the displaying step is realized.

For example, here, the adequate output device may be the output device 33 disposed in the information processing section 13, an output device disposed in a device other than the information processing section 13 such as an output device (not shown) which is different from the output device 26, and which is disposed in the body motion signal detecting apparatus 10, or an output device which is, for example, a monitor that is possessed by the subject of Parkinson's disease or the like, the family member, or the doctor, and which is outside the information processing section 13.

Namely, the adequate output device functions as an output section which outputs a result extracted by the information processing section 13, and further as a display device including a display section which displays a result obtained by the information processing apparatus.

In the case where the correctly obtained rhythm cycle is to be displayed on the output device such as an output device which is different from the output device 26, and which is disposed in the body motion signal detecting apparatus 10, or a monitoring device which is possessed by the subject of Parkinson's disease or the like, the family member, or the doctor, for example, the information processing section 13 transmits the correctly obtained rhythm cycle through wired or wireless connection, or a recording medium such as a medium, to the output device such as the output device which is different from the output device 26, and which is disposed in the body motion signal detecting apparatus 10, or a monitoring device which is possessed by the subject of Parkinson's disease or the like, the family member, or the doctor.

Namely, a result extracted by the information processing apparatus is transmitted to the subject through the body motion signal detecting apparatus. In other words, the output device which is different from the output device 26, and which is disposed in the body motion signal detecting apparatus 10 functions as a transmission section which transmits a result extracted by the information processing apparatus to the subject.

The function of transmitting the correctly obtained rhythm cycle is realized by various well-known techniques, for example, by execution of programs stored in the storage device 32 by the central processing unit 31. Preferably, the output value output by the adequate output device may be output as the time dependency of the rhythm cycle or correlation with the amount of activity.

The information processing section 13 can perform also a process of evaluating Parkinson's disease in the following manner. Specifically, for example, the central processing unit 31 disposed in the information processing section 13 executes a program stored in the storage device 32 to function as the evaluation section 314.

Namely, the evaluation section 314 executes, for example, as the evaluating step, a comparing step, first analyzing step, second analyzing step, third analyzing step, fourth analyzing step, fifth analyzing step, first outputting step, second outputting step, third outputting step, and fourth outputting step which will be described later.

Another information processing apparatus which is separated from the information processing section 13, and which includes a central processing unit, a storage device, and the like may execute a predetermined program, thereby realizing the evaluation section 314. In this case, for example, the information processing section 13 transmits the correctly obtained rhythm cycle to the other information processing apparatus through wired or wireless connection, or a recording medium such as a medium, and the evaluation section 314 of the other information processing apparatus performs a process of evaluating Parkinson's disease based on the information.

Namely, the information processing section 13 or the evaluation section 314 of the other information processing apparatus functions as an evaluation device which evaluates the severity of Parkinson's disease, and which is attached to the information processing section 13. Here, the terms of the evaluating device which is attached to the information processing section 13 indicate that the evaluation device exists in the information processing section 13, and that the evaluation device is connected to the information processing section 13.

For example, the gait rhythm cycle (gait rhythm) which is calculated from the gait rhythm, or its average value is compared in time series (the comparing step), and, when the rhythm cycle or its average value begins to be reduced, information indicating it, or the like is output and displayed, for example, on the output device 33 (the first outputting step).

Conversely, when the rhythm cycle or its average value which has been reduced is increased to return to its original level, information indicating it, or the like is output and displayed, for example, on the output device 33 (the second outputting step).

When the rhythm cycle or the like begins to be reduced, for example, information indicating it is output to the output section (the third outputting step), and the output section notifies to the patient, the doctor, and the like. When the notification is performed, for example, the patient can take a medicine. When an occurrence of an abnormality is notified to a potential patient of Parkinson's disease who is not undergoing diagnosis or treatment by a doctor, or the family member, the patient can take adequate action such as going to a hospital.

After taking a medicine, the biological signal information may be further analyzed, and, when the rhythm cycle or its average value becomes a normal level and is stabilized, it may be determined that the medicine has a medicinal effect (the first analyzing effect), and information indicating it or the like may be similarly output to the output section (the fourth outputting step). When the output section performs notification to the patient or the like, the patient can feel a sense of ease indicating that the pathological condition is stable.

Based on the time variation of the rhythm cycle or its average, the information processing section 13 can evaluate also the time change of the pathological condition. The time change of the pathological condition means, for example, that the pathological condition changes depending on the time of a day.

When the time change of the pathological condition is analyzed based on the time variation (the second analyzing step), the patient, the doctor, and the like can know, for example, that symptoms easily appear in which one of time periods of 24 hours.

The information processing section 13 may determine (the third analyzing step) the severity of Parkinson's disease based on a time variation pattern of the rhythm cycle in a predetermined time period. Specifically, or the time change of the rhythm cycle or the average value of the rhythm cycle is tracked for a long time period, for example, 10 or more hours.

When the gait cycle is substantially constant and less fluctuates, it is determined that the severity is low and the pathological condition is stable.

In the case where the gait cycle largely fluctuates and the large fluctuation is caused by medication, i.e., the case where the gait cycle is increased (or decreased) by medication and, when the medicinal effect disappears, the gait cycle is decreased (or increased), it is determined that symptom is not mild but is well controlled.

In the case where the gait cycle largely fluctuates irrespective of the timing of medication, it can be determined that the pathological condition is poorly controlled.

The information processing section 13 may evaluate the state of Parkinson's disease based on the rhythm cycle and the waveform of the rhythm. In the example, particularly, the information processing section 13 preferably has a function of detecting a sudden abnormality of the rhythm cycle of the repetitive rhythmic motion based on the rhythm cycle and the waveform of the rhythm.

Also such a detection of a sudden abnormality of the rhythm cycle can be performed, for example, in the central processing unit 31 in the information processing section 13, by calculating and processing data input from the information collection section 12, and data and the like stored in the storage device 32 of the information processing section 13.

Figure 15:
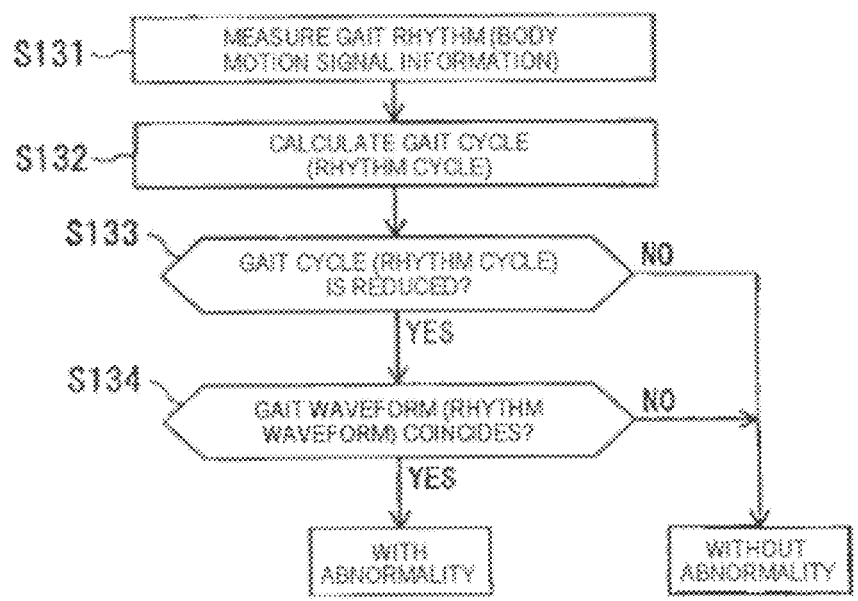
FIG. 15 is a flowchart illustrating an example of a method of detecting a sudden rhythm abnormality of a repetitive rhythmic motion in an evaluating apparatus for Parkinson's disease which is an embodiment of the invention.

A method of detecting a sudden abnormality of the rhythm (gait rhythm) cycle will be described with reference to the flowchart of FIG. 15.

The body motion signal detection section 11 measures, for example, the gait rhythm as the body motion signal information (step S131), and data are recorded and stored in the information collection section 12.

The information processing section 13 acquires data from the information collection section 12, and obtains the rhythm cycle from the rhythm waveform (step S132).

The way of obtaining the rhythm cycle is as described above. The information processing section 13 analyzes the rhythm cycle which changes every moment, and determines whether the rhythm cycle is largely reduced or not (step S133: the fourth analyzing step).

If a large reduction of the rhythm cycle is not observed (see NO route from step S133), it is determined that there is no sudden abnormality of the rhythm.

If a reduction of the rhythm cycle is observed (see YES route from step S133), it is further determined whether the rhythm waveform coincides with a predetermined waveform or not (step S134: the fifth analyzing step).

If the rhythm waveform is consistent with the predetermined waveform (see YES route from step S134), it is determined that there is a sudden abnormality.

As the predetermined waveform, for example, a waveform due to an abnormal gait such as a small-step gait may be employed. A waveform which is observed commonly in Parkinson's disease, or an abnormal gait waveform which is unique to a patient may be previously stored in the information processing section 13 or a storage section or the like (for example, the storage device 32) disposed in the evaluation device, as a database.

By contrast, if the rhythm waveform is not consistent with the predetermined waveform (see NO route from step S134), it is determined that there is no abnormality.

Figure 16:
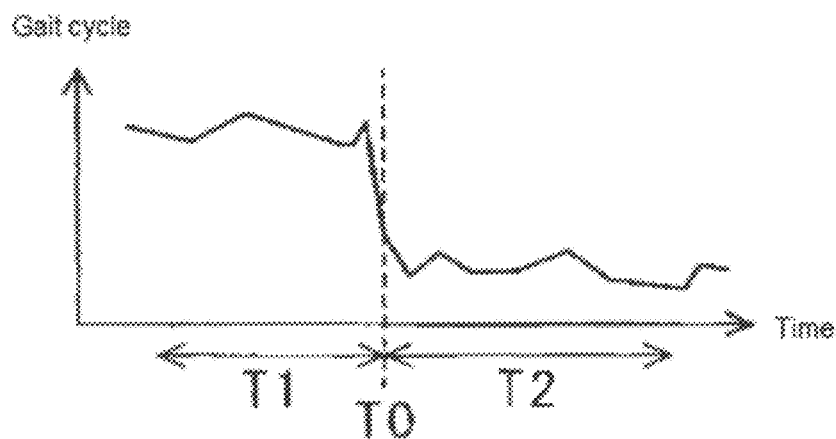
FIG. 16 is a graph illustrating an example of a method of detecting a sudden rhythm abnormality of a repetitive rhythmic motion in the evaluating apparatus for Parkinson's disease which is an embodiment of the invention.

Here, the method of determining a reduction of the gait cycle in step S133 may be, for example, the following method. The method will be described with reference to FIG. 16.

In the case where it is determined at certain time T0 whether there is a reduction of the rhythm cycle or not, an average value M1 of the gait rhythm cycle within a predetermined period T1 previous to T0 is obtained. Next, an average value M2 of the gait rhythm cycle within a predetermined period T2 subsequent to T0 is obtained.

As T1 and T2, time periods of an adequate length are set. For example, the time periods may be set to a value which is equal to or more than 1 sec. and equal to or less than 10 sec. If a relationship of $M2<M1\times\alpha$ is established between the thus obtained average values M1 and M2 of the gait rhythm cycle and with using a predetermined coefficient $\alpha$ ($0<\alpha<1$), it is determined that there is a reduction of the gait rhythm cycle.

In step S134, it may be further determined that the gait waveform is consistent with or very similar to a predetermined waveform by using, for example, a known pattern matching technique.

When a mode in which, in the case where the occurrence of such a sudden abnormality is detected by the information processing section 13, the occurrence of the abnormality is notified in real time to the patient by the output section or the like is employed, the patient who receives the notification can take an adequate measure such as that the patient immediately takes a medicine, or that the patient refrains from exercise.

Examples of a medicine for Parkinson's disease are L-DOPA, an anticholinergic agent, amantadine hydrochloride, ergot and non-ergot alkaloids, selegiline hydrochloride, and L-DOPS.

When a mode in which the time period and frequency in which a sudden abnormality appears are notified to the doctor is employed, the doctor can correctly know the diurnal variation and severity of the pathological condition of the patient. When an occurrence of an abnormality is notified to a potential patient of Parkinson's disease who is not undergoing diagnosis or treatment by a doctor, or the family member, the patient can take adequate action such as going to a hospital.

The output section is not particularly limited as far as it can notify the patient or the doctor of a result evaluated by the information processing section 13, and the like. For example, a configuration in which a state change or a sudden abnormality is notified by means of an alarm, vibrations, or the like may be employed, or that in which an evaluation result of the time variation or severity of the pathological condition is displayed on a display may be employed.

The output section may be an independent device, or disposed in a predetermined device or the like. For example, the output section may be disposed in the body motion signal detecting apparatus 10, or in the information processing section 13. Alternatively, the output device 33 may be used as the output section.

The information processing section 13 transmits information indicating an occurrence of the abnormality or the like through, for example, wired or wireless connection.

(Others)

When the nervous system, muscles, skeleton, or the like related to a gait has impairment, an abnormality occurs in a gait. From the state of gait impairment, therefore, it is possible to specify the cause of the gait impairment, or diagnose or evaluate the disease. In other words, from the gait rhythm cycle, it is possible to specify the cause of the gait impairment, or diagnose or evaluate the disease.

When the gait rhythm cycle is accurately measured, therefore, it is possible to diagnose or evaluate various illnesses or diseases which cause impairment in the nervous system, muscles, skeleton, and the like related to a gait, such as, in addition to Parkinson's disease, stroke, spinal cord injury, cerebral palsy, myelodysplasia, muscular dystrophy, osteoarthritis, rheumatoid arthritis, multiple sclerosis, alcoholic intoxication, dementia, and hydrocephalus.

Various programs for realizing the functions of the central processing unit 31 and the like included in the information processing section 13 are provided in the form in which the programs are recorded on a recording medium which is readable by a computer, such as a flexible disk, a CD (for example, a CD-ROM, a CD-R, or a CD-RW), a DVD (for example, a DVD-ROM, a DVD-RAM, a DVD-R, a DVD+R, a DVD-RW, a DVD+RW, or an HD-DVD), a Blu-ray disk, a magnetic disk, an optical disk, or a magnetooptical disk.

Then, the computer reads the programs from the recording medium, and uses the programs after transferring and storing the programs to an internal or external storage device. Alternatively, the programs may be recorded in a storage device (recording medium) such as a magnetic disk, an optical disk, or a magnetooptical disk, and provided from the storage device to the computer, through a communication channel.

In the embodiment, the computer indicates a concept including hardware and an operating system, and means hardware which operates under control of an operating system.

In the case where an operating system is unnecessary and hardware is caused to operate by an application program alone, the hardware itself corresponds to the computer. The hardware includes at least a microprocessor such as a central processing unit, and means for reading computer programs recorded on a recording medium. In the embodiment, the information processing section 13 has a function as a computer including the central processing unit 31.

EXAMPLES

Although, hereinafter, the invention will be described in further detail with reference to examples, the invention is not limited to the following examples without departing from the spirit thereof.

Example 1

A body motion of a patient of Parkinson's disease who can stably walk without support was measured by a portable acceleration measuring apparatus (8×6×2 cm). As the measuring apparatus, an apparatus in which a three-axis acceleration sensor (the measuring range of ±5 G) is mounted as the body motion signal detection section 11 was used. The acceleration waveform was recorded by attaching a mini SD card (an information collection section) to the body of the measuring apparatus. This was attached to the waist of the subject while being inserted in a secret belt, and the measurement was conducted at a sampling frequency of 100 Hz.

The reference wave having a width of 500 msec. was selected from obtained three-axis acceleration time-series data x(t), y(t), and z(t), and the cycle candidate extracting step by the autocorrelation method, and the auxiliary-wave producing step were applied to select a true rhythm cycle.

FIG. 17 shows a part of a time-series graph. FIG. 17A shows a plot of an absolute value of the acceleration, and FIG. 17B shows the extracted rhythm cycle candidates and auxiliary wave.

As shown in FIG. 17A, the cycle of the rhythm cycle candidate wave which has the maximum peak in the auxiliary wave was selected as a true rhythm cycle [the symbol of * in FIG. 17A]. It was confirmed that the selected rhythm cycle coincides with the actual gait rhythm cycle. Therefore, it was seen that the gait rhythm cycle can be correctly selected by the method of the invention.

Comparative Example 1

A determining method which uses a threshold, and which is conventionally often employed was applied to the rhythm cycle candidates obtained in Example 1 to select the rhythm cycle (FIG. 18). FIG. 18A shows a plot of an absolute value of the acceleration, and FIG. 18B shows the extracted rhythm cycle candidates and the threshold.

As shown in FIG. 18B, the rhythm cycle candidates which exceed the threshold line were selected as a rhythm cycle. In this method, the cycle of the rhythm cycle candidate having the peak of the symbol of x in FIG. 18B was selected as an erroneous peak position. When the threshold was increased in order to eliminate the symbol of x, also several true rhythm cycles to be selected were eliminated. Anyway, a true rhythm cycle could not be selected by the threshold method.

Example 2

Figures 19A, 19B:
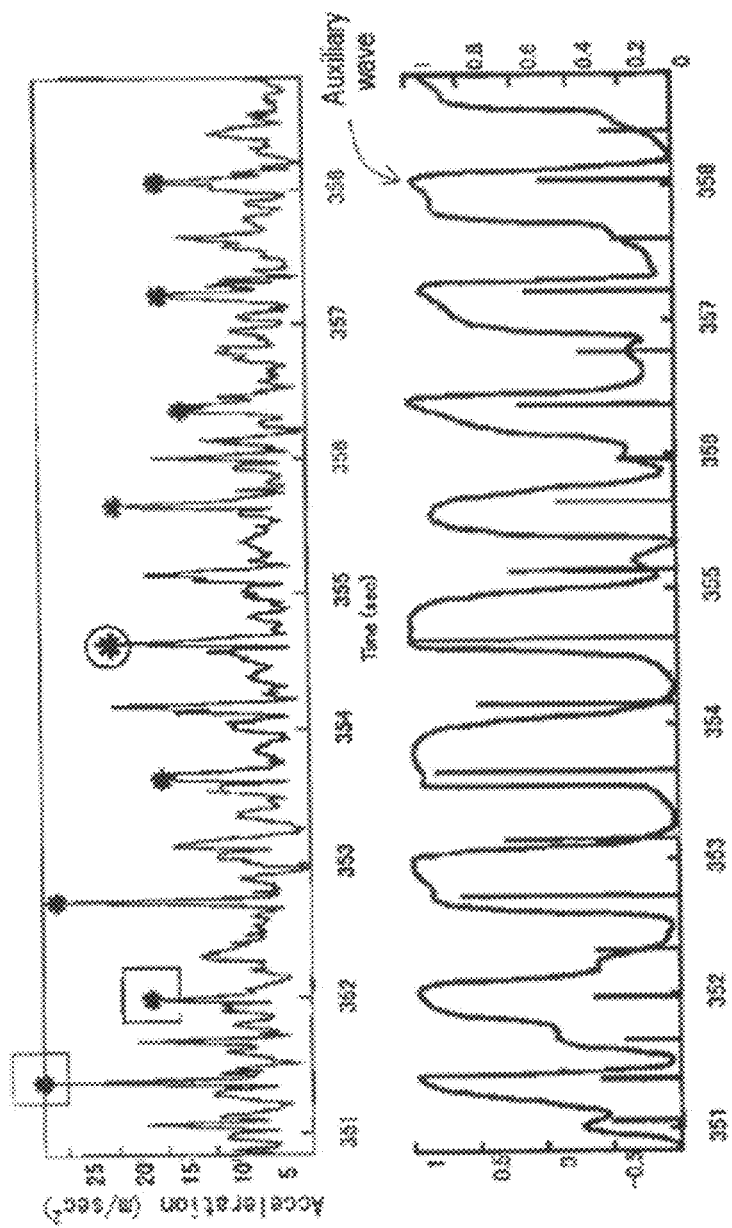
FIGS. 19A and 19B are graphs in which peak positions of a gait rhythm are selected in Embodiment 2 of the invention.

In a procedure similar to that of Example 1, a body motion of a patient of Parkinson's disease who can stably walk without support was measured (FIG. 19). The reference wave having a width of 500 msec. [in FIGS. 19A and 20A, the center position is indicated by the symbol ○] was selected, and rhythm cycle candidates were extracted by the autocorrelation method [FIG. 19B]. As shown in FIG. 19B, then, an auxiliary wave was produced, and a rhythm cycle which has the peak positions having the maximum autocorrelation coefficient was selected from the portion surrounded by the auxiliary wave, as a true rhythm cycle [the symbol of * in FIG. 19A].

As shown in FIG. 19B, it was seen that peaks are correctly decided. Particularly, two peaks which have a low correlation value with respect to the reference wave, and which are indicated by a symbol of □ in FIG. 19A were correctly selected. The rhythm cycle candidate wave having the peaks shows a low correlation with the reference wave because the manner of walking was suddenly changed at time 352 seconds. Therefore, it is seen that, according to the method of the invention, it is possible to accurately detect the gait rhythm cycle following such a sudden change of the gait pace.

Comparative Example 2

Waves which are centered at the rhythm cycle candidates extracted in Example 2, respectively, and which have a width of 500 msec. were taken out, and mutual correlation coefficients were calculated by the autocorrelation method. In this way, the degrees of similarity (in statistical terms, the distances) between peaks in all the rhythm cycle candidates are obtained. Based on the values, a clustering analysis was performed by the K-means method (Seber, G. A. F. Multivariate Observations. Hoboken, N.J.: John Wiley & Sons, Inc. 1984) (FIG. 20). Peaks selected by this are shown in FIG. 20B. From FIG. 20B, it was seen that the rhythm cycle was not correctly obtained.

Example 3

In a procedure similar to that of Example 1, a body motion of one day of a patient of Parkinson's disease who shows freezing of gait was measured. A scale was obtained every one second from an acceleration signal. Based on the scale, extraction of rhythm cycle candidates, and production of an auxiliary wave were performed, and, from information of the both, peak positions of the gait were decided. The gait rhythm cycle for each step was calculated from the interval of adjacent peak positions. With respect to the thus obtained gait cycles, an average value was obtained at five-minute intervals. An average of absolute values of accelerations during the gait was obtained similarly at five-minute intervals. Absolute values of accelerations provide good indications of the amount of activity of a human.

The symbols of * in FIGS. 21A and 21B show plots of the correlation between the both (an approximate curve is shown by the solid line). The broken line shows a line of a healthy person. In the normal gait, when the gait cycle is shortened, the acceleration of the gait is increased, and therefore a downward-sloping curve is obtained.

FIG. 21A indicates a result of measurements on the patient before administration of Levodopa, and shows that the result was largely deviated from the line of a healthy person. By contrast, FIG. 21B indicates a result of measurements after Levodopa was administered for about one month and the symptom was improved, and shows that the result was close to the line of a healthy person. Therefore, it is seen that, according to the method of the invention, the correlation between the correctly obtained rhythm cycle and the amount of activity is visually displayed, and therefore the state of Parkinson's disease and the medicinal effect can be adequately known.

Example 4

Figures 22A, 22B:
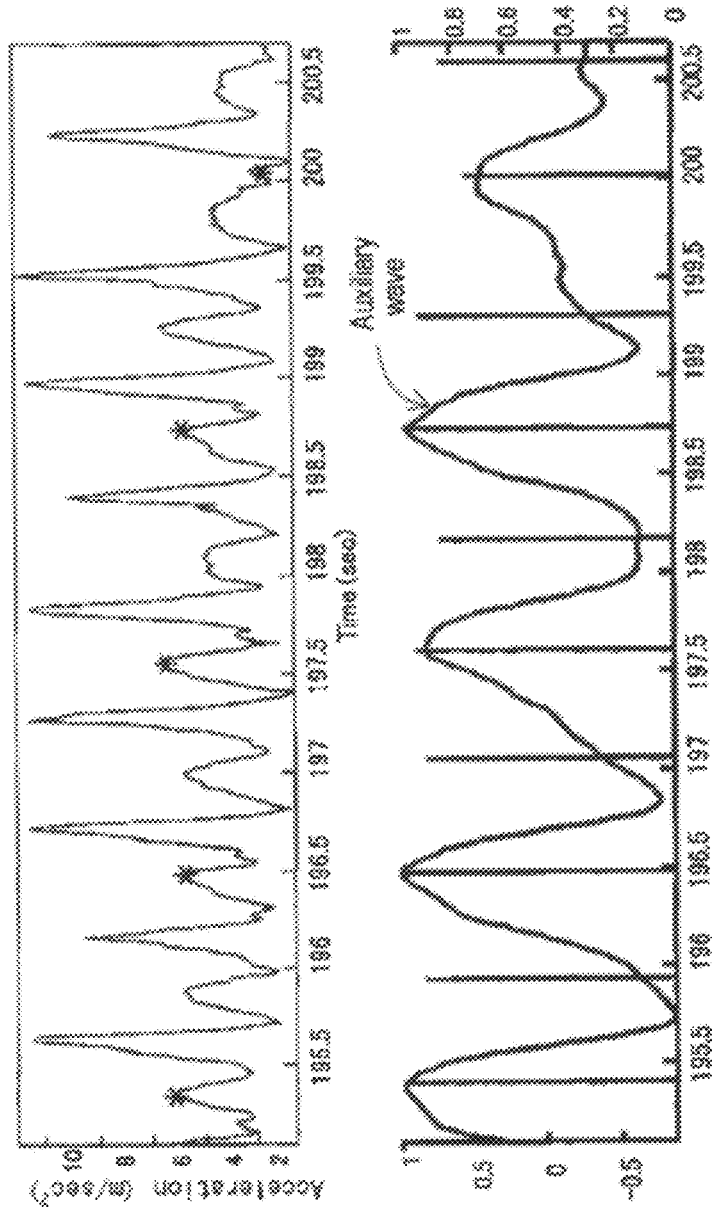
FIGS. 22A and 22B are graphs in which peak positions of a gait rhythm are selected in Embodiment 4 of the invention.

The acceleration was measured at 100 Hz when a walk was made while the measuring apparatus was placed in a knapsack and the knapsack was slung over the right shoulder (FIG. 22). From an absolute value acceleration waveform [FIG. 22A] and the autocorrelation coefficient [FIG. 22B], it is impossible to distinguish the gait performed by the same foot.

Also in this case, as shown in FIG. 22A, when an auxiliary wave was considered, it was possible to select the correct rhythm cycle [the symbol of * in FIG. 22A]. Therefore, it was seen that, according to the method of the invention, the gait rhythm cycle can be accurately measured irrespective of the attached portion of the device.

Example 5

The acceleration was measured at 100 Hz when a walk of eleven steps starting with the right foot was made while the measuring apparatus was attached to the middle of the abdomen. A waveform which was obtained by performing −1-time integration (i.e., differential) on the acceleration signal in the lateral direction was set as the motion trajectory, an auxiliary wave based on an anisotropy evaluation was produced, and the gait peak was decided (FIG. 23).

FIG. 23A shows an example of the acceleration signal in the lateral direction, and FIG. 23B shows an example of the auxiliary wave based on an anisotropy evaluation and candidates of the rhythm cycle which were obtained from the acceleration signal in the lateral direction shown in FIG. 23A. As shown in FIG. 23A, it was possible to correctly extract the gait peak due to left foot steps [the symbol of * in FIG. 23A].

Next, a waveform which was obtained by performing 1-time integration on the above-described acceleration signal was set as the motion trajectory, an auxiliary wave based on an anisotropy evaluation was produced, and the gait peak was decided (FIG. 24). FIG. 24A shows an example of the acceleration signal in the lateral direction, and FIG. 24B is a view showing an example of the auxiliary wave based on an anisotropy evaluation and candidates of the rhythm cycle which were obtained from the acceleration signal in the lateral direction shown in FIG. 24A.

As shown in FIG. 24A, it was possible to correctly extract the gait peak due to right foot steps [the symbol of * in FIG. 24A].

In both cases where the acceleration signal underwent −1-time integration and 1-time integration, when a wave which was obtained by vertically inverting the auxiliary wave was set to a new auxiliary wave, it was possible to select also a peak based on steps of the opposite foot.

From these results, it was seen that, according to the method of the invention, the use of a wave of the −1- or 1-time integration enables right and left steps to be discriminated (identified).

Although the invention has been described in detail and with reference to the specific embodiments, it is obvious to those skilled in the art that various changes and modifications can be made without departing from the spirit and scope of the invention.

The present invention may include the following configurations.

1. An information processing method for a body motion signal in an information processing apparatus for performing information processing on body motion signal information which is obtained by an operation in which a subject carries a body motion signal detecting apparatus having a body motion signal detection section that measures non-invasively and continuously at least a repetitive rhythmic motion of a human body and for extracting a result obtained in the information processing, the information processing including following steps of (1) to (3):

(1) a cycle candidate extracting step of applying a pattern matching process on the body motion signal information, and extracting a rhythm cycle candidate wave as rhythm cycle candidates related to the rhythmic motion;

(2) an auxiliary-wave producing step of performing −1 or more times integration on the body motion signal information to obtain a motion trajectory, and performing coarse-graining on the motion trajectory to produce an auxiliary wave; and (3) a cycle selecting step of superimposing the rhythm cycle candidate wave which is extracted in the cycle candidate extracting step, on the auxiliary wave which is obtained in the auxiliary wave producing step, and selecting a cycle of a rhythm cycle candidate wave which has a peak in the auxiliary wave, as a true cycle.

2. The information processing method for the body motion signal according to the item 1, wherein,
in the cycle selecting extracting step, a cycle of a rhythm cycle candidate wave which has a maximum peak in the auxiliary wave is selected as the true cycle.

3. The information processing method for the body motion signal according to the item 1 or 2, wherein
the body motion signal information is acceleration signal information of a body motion which is obtained by a three-axis acceleration sensor serving as the body motion signal detection section.

4. The information processing method for the body motion signal according to any one of the items 1 to 3, wherein
the information processing apparatus is disposed separately from the body motion signal detecting apparatus,
the body motion signal detecting apparatus includes an information collection section which is disposed detachably from the body motion signal detecting apparatus, and which records the body motion signal information,
the information processing apparatus includes an information import section which imports the body motion signal information recorded in the information collection section, and
the body motion signal information recorded in the information collection section which is detached from the body motion signal detecting apparatus, and in which the body motion signal information is recorded are imported through the information import section of the information processing apparatus.

5. The information processing method for the body motion signal according to any one of the items 1 to 3, wherein
the information processing apparatus is disposed separately from the body motion signal detecting apparatus,
the body motion signal detecting apparatus includes an information collection section which records the body motion signal information,
the information processing apparatus includes an information import section which imports the body motion signal information recorded in
the information collection section through communicating means, and the body motion signal information is once stored in the information collection section, and then transmitted to the information import section of the information processing apparatus through the communicating means.

6. The information processing method for the body motion signal according to any one of the items 1 to 5, wherein
the information processing apparatus is disposed separately from the body motion signal detecting apparatus, and
the result extracted by the information processing apparatus is transmitted to the subject through the body motion signal detecting apparatus.

7. The information processing method for the body motion signal according to any one of the items 1 to 6, wherein the repetitive rhythmic motion is a gait.

8. The information processing method for the body motion signal according to any one of the items 1 to 7, wherein a severity of Parkinson's disease is evaluated from the result extracted by the information processing apparatus.

9. An information processing system for a body motion signal, the information processing system including:

a body motion signal detecting apparatus which detects body motion signal information by a body motion signal detection section that measures non-invasively and continuously at least a repetitive rhythmic motion of a human body by an operation in which a subject carries the body motion signal detection section; and an information processing apparatus which performs information processing on the body motion signal information obtained in the body motion signal detecting apparatus and extracts a result obtained by the information processing, wherein the information processing apparatus includes:

a cycle candidate extraction section which applies a pattern matching process on the body motion signal information to extract a rhythm cycle candidate wave as rhythm cycle candidates related to the rhythmic motion;

an auxiliary-wave production section which performs −1 or more times integration on the body motion signal information to obtain a motion trajectory, and which performs coarse-graining on the motion trajectory, thereby producing an auxiliary wave; and a cycle selection section which superimposes the rhythm cycle candidate wave that is extracted by the cycle candidate extraction section, on the auxiliary wave that is produced by the auxiliary-wave production section, and which selects a cycle of a rhythm cycle candidate wave that has a peak in the auxiliary wave, as a true cycle.

10. The information processing system for the body motion signal according to the item 9, wherein the cycle selection section selects a cycle of a rhythm cycle candidate wave that has a maximum peak in the auxiliary wave, as the true cycle.

11. The information processing system for the body motion signal according to the item 9 or 10, wherein the information processing apparatus is disposed separately from the body motion signal detecting apparatus, the body motion signal detecting apparatus includes an information collection section which is disposed detachably from the body motion signal detection section, and which records the body motion signal information, and the information processing apparatus includes an information import section which imports, for the information processing, the body motion signal information from the information collection section which is detached from the body motion signal detecting apparatus, and in which the body motion signal information is recorded.

12. The information processing system for the body motion signal according to the item 9 or 10, wherein the body motion signal detecting apparatus and the information processing apparatus are connected to each other through communicating means, the body motion signal detecting apparatus includes an information collection section which records the body motion signal information, and the information processing apparatus includes an information import section which imports the body motion signal information that is transmitted through the communicating means, and that is stored in the information collection section.

13. The information processing system for the body motion signal according to any one of the items 9 to 12, wherein the body motion signal detecting apparatus is disposed separately from the information processing apparatus, and the body motion signal detecting apparatus includes a transmission section which transmits the result extracted by the information processing apparatus to the subject.

14. The information processing system for the body motion signal according to the item 9 or 10, wherein the body motion signal detecting apparatus is disposed integrally with the information processing apparatus, and configured to be portable with the subject.

15. The information processing system for the body motion signal according to any one of the items 9 to 14, including an output section which outputs the result extracted by the information processing apparatus.

16. The information processing system for the body motion signal according to any one of the items 9 to 15, including an evaluating apparatus which evaluates a severity of Parkinson's disease from the result extracted by the information processing apparatus.

17. An information processing apparatus for performing information processing on a body motion signal which is obtained by an operation in which a subject carries a body motion signal detecting apparatus including a body motion signal detection section that measures non-invasively and continuously at least a repetitive rhythmic motion of a human body, and for extracting a result obtained by the information processing, the information processing apparatus including:

a cycle candidate extraction section which applies a pattern matching process on the body motion signal information to extract a rhythm cycle candidate wave that is rhythm cycle candidates related to the rhythmic motion;

an auxiliary-wave production section which performs −1 or more times integration on the body motion signal information to obtain a motion trajectory, and which performs coarse-graining on the motion trajectory, thereby producing an auxiliary wave; and a cycle selection section which superimposes the rhythm cycle candidate wave that is extracted by the cycle candidate extraction section, on the auxiliary wave that is produced by the auxiliary-wave production section, and which selects a cycle of a rhythm cycle candidate wave that has a peak in the auxiliary wave, as a true cycle.

18. The information processing apparatus for the body motion signal according to the item 17, wherein the cycle selection section selects a cycle of a rhythm cycle candidate wave that has a maximum peak in the auxiliary wave, as the true cycle.

19. The information processing apparatus for the body motion signal according to the item 17 or 18, wherein an evaluation device which evaluates a severity of Parkinson's disease from the result extracted by the information processing apparatus is attached to the information processing apparatus.

20. A displaying apparatus, including a display section which displays the result obtained in the information processing apparatus as defined in the item 17.

21. A displaying method, including a displaying step of displaying the result obtained in the information processing apparatus as defined in the item 17, on a display section.

22. A computer-readable recording medium which records a program to be used in an information processing method for a body motion signal in an information processing apparatus for performing information processing including desired process steps on body motion signal information which is obtained by an operation in which a subject carries a body motion signal detecting apparatus having a body motion signal detection section that measures non-invasively and continuously at least a repetitive rhythmic motion of a human body, and for extracting a result obtained in the information processing, the program causing a computer to execute:

a cycle candidate extracting step of applying a pattern matching process on the body motion signal information, and extracting a rhythm cycle candidate wave as rhythm cycle candidates related to the rhythmic motion;

an auxiliary-wave producing step of performing −1 or more times integration on the body motion signal information to obtain a motion trajectory, and performing coarse-graining on the motion trajectory to produce an auxiliary wave; and a cycle selecting step of superimposing the rhythm cycle candidate wave which is extracted in the cycle candidate extracting step, on the auxiliary wave which is obtained in the auxiliary wave producing step, and selecting a cycle of a rhythm cycle candidate wave which has a peak in the auxiliary wave, as a true cycle.

23. The computer-readable recording medium according to the item 22, wherein, the computer is caused to execute the cycle selecting step in which a cycle of a rhythm cycle candidate wave which has a maximum peak in the auxiliary wave is selected as the true cycle.

24. A program which is to be used in an information processing method for a body motion signal in an information processing apparatus for performing information processing including desired process steps on body motion signal information which is obtained by an operation in which a subject carries a body motion signal detecting apparatus having a body motion signal detection section that measures non-invasively and continuously at least a repetitive rhythmic motion of a human body, and extracting a result obtained in the information processing, the program causing a computer to execute:

a cycle candidate extracting step of applying a pattern matching process on the body motion signal information, and extracting a rhythm cycle candidate wave as rhythm cycle candidates related to the rhythmic motion;

an auxiliary-wave producing step of performing −1 or more times integration on the body motion signal information to obtain a motion trajectory, and performing coarse-graining on the motion trajectory to produce an auxiliary wave; and a cycle selecting step of superimposing the rhythm cycle candidate wave which is extracted in the cycle candidate extracting step, on the auxiliary wave which is obtained in the auxiliary wave producing step, and selecting a cycle of a rhythm cycle candidate wave which has a peak in the auxiliary wave, as a true cycle.

25. The program according to the item 24, wherein the computer is caused to execute the cycle selecting step in which a cycle of a rhythm cycle candidate wave which has a maximum peak in the auxiliary wave is selected as the true cycle.

26. A body motion signal detecting apparatus which is to be used in the information processing method for the body motion signal as defined in the item 1.

27. A method of detecting a body motion signal for obtaining a body motion signal to be used in the information processing method for the body motion signal as defined in the item 1.

28. An outputting apparatus which is used for outputting the result obtained by the information processing method for the body motion signal as defined in the item 1.

29. An outputting method for outputting the result obtained by the information processing method for the body motion signal as defined in the item 1.

30. A diagnosing method of diagnosing an illness in an information processing apparatus for performing information processing on body motion signal information which is obtained by an operation in which a subject carries a body motion signal detecting apparatus having a body motion signal detection section that measures non-invasively and continuously at least a repetitive rhythmic motion of a human body and for extracting a result obtained in the information processing, the information processing including following steps of (1) to (3):

(1) a cycle candidate extracting step of applying a pattern matching process on the body motion signal information, and extracting a rhythm cycle candidate wave as rhythm cycle candidates related to the rhythmic motion;

(2) an auxiliary-wave producing step of performing −1 or more times integration on the body motion signal information to obtain a motion trajectory, and performing coarse-graining on the motion trajectory to produce an auxiliary wave; and (3) a cycle selecting step of superimposing the rhythm cycle candidate wave which is extracted in the cycle candidate extracting step, on the auxiliary wave which is obtained in the auxiliary wave producing step, and selecting a cycle of a rhythm cycle candidate wave which has a peak in the auxiliary wave, as a true cycle.

31. The diagnosing method according to the item 30, wherein the illness is any one of Parkinson's disease, stroke, spinal cord injury, cerebral palsy, myelodysplasia, muscular dystrophy, osteoarthritis, rheumatoid arthritis, multiple sclerosis, alcoholic intoxication, dementia, and hydrocephalus.

32. The diagnosing method according to the item 30, wherein the illness is Parkinson's disease, and a severity of Parkinson's disease is evaluated from the result extracted by the information processing apparatus.

33. A diagnosing system for diagnosing an illness, the diagnosing system including:

a body motion signal detecting apparatus which detects body motion signal information by a body motion signal detection section that measures non-invasively and continuously at least a repetitive rhythmic motion of a human body by an operation in which a subject carries the body motion signal detection section; and an information processing apparatus which performs information processing on the body motion signal information obtained in the body motion signal detecting apparatus, wherein the information processing apparatus includes:

a cycle candidate extraction section which applies a pattern matching process on the body motion signal information to extract a rhythm cycle candidate wave as rhythm cycle candidates related to the rhythmic motion;

an auxiliary-wave production section which performs −1 or more times integration on the body motion signal information to obtain a motion trajectory, and which performs coarse-graining on the motion trajectory, thereby producing an auxiliary wave; and a cycle selection section which superimposes the rhythm cycle candidate wave that is extracted by the cycle candidate extraction section, on the auxiliary wave that is produced by the auxiliary-wave production section, and which selects a cycle of a rhythm cycle candidate wave that has a peak in the auxiliary wave, as a true cycle.

34. The diagnosing system according to the item 33, wherein the illness is any one of Parkinson's disease, stroke, spinal cord injury, cerebral palsy, myelodysplasia, muscular dystrophy, osteoarthritis, rheumatoid arthritis, multiple sclerosis, alcoholic intoxication, dementia, and hydrocephalus.

35. The diagnosing system according to the item 33, wherein the illness is Parkinson's disease, and the diagnosing system includes an evaluating apparatus which evaluates a severity of Parkinson's disease from the result extracted by the information processing apparatus.

36. A diagnosing apparatus for diagnosing an illness for performing information processing on body motion signal information which is obtained by an operation in which a subject carries a body motion signal detecting apparatus having a body motion signal detection section that measures non-invasively and continuously at least a repetitive rhythmic motion of a human body, and for extracting a result obtained by the information processing, the diagnosing apparatus including:

a cycle candidate extraction section which applies a pattern matching process on the body motion signal information to extract a rhythm cycle candidate wave as rhythm cycle candidates related to the rhythmic motion;

an auxiliary-wave production section which performs −1 or more times integration on the body motion signal information to obtain a motion trajectory, and which performs coarse-graining on the motion trajectory, thereby producing an auxiliary wave; and a cycle selection section which superimposes the rhythm cycle candidate waves that are extracted by the cycle candidate extraction section, on the auxiliary wave that is produced by the auxiliary-wave production section, and which selects a cycle of a rhythm cycle candidate wave that has a peak in the auxiliary wave, as a true cycle.

What is claimed is:

1. An information processing method implemented on a central processing unit or microprocessor to perform information processing in an information processing apparatus that includes the central processing unit or microprocessor the information processing method including steps of:

obtaining body motion signal information from a body motion signal formed by an operation in which a subject carries a body motion signal detecting apparatus, the body motion signal detection apparatus being mounted on, connected to, or housed on the subject and having a body motion signal detection section that measures non-invasively and continuously at least a repetitive rhythmic motion of a human body the subject;

applying a pattern matching process, in a cycle candidate extracting step, on the body motion signal information, and extracting a rhythm cycle candidate wave as rhythm cycle candidates related to the rhythmic motion;

performing −1 or more times integration, in an auxiliary-wave producing step, on the body motion signal information to obtain a motion trajectory, determining a time scale from the motion trajectory, and performing coarse-graining on the motion trajectory by using the time scale of the motion trajectory to produce an auxiliary wave; and superimposing, by implementing the superimposing on the central processing unit or the microprocessor of the information processing apparatus in a cycle selecting step, the rhythm cycle candidate wave, that was extracted in the cycle candidate extracting step, on the auxiliary wave, that was obtained in the auxiliary-wave producing step, and selecting a cycle of the rhythm cycle candidate wave which has a peak in a region surrounded by a peak of the auxiliary wave, as a true cycle.

2. The information processing method for the body motion signal according to claim 1, wherein, in the cycle selecting step, a cycle of the rhythm cycle candidate wave that has a maximum peak in the region surrounded by a peak of the auxiliary wave is selected as the true cycle.

3. The information processing method for the body motion signal according to claim 1, wherein the body motion signal information is acceleration signal information of a body motion which is obtained by a three-axis acceleration sensor serving as the body motion signal detection section.

4. The information processing method for the body motion signal according to claim 1, wherein the information processing apparatus is disposed in a first housing separately from the body motion signal detecting apparatus, the body motion signal detecting apparatus includes an information collection section that records the body motion signal information, the information collection section being detachable from the body motion signal detecting apparatus, the information processing apparatus includes an information import section that imports the body motion signal information recorded in the information collection section, and the body motion signal information recorded in the information collection section, which is detachable from the body motion signal detecting apparatus, is imported through the information import section of the information processing apparatus.

5. The information processing method for the body motion signal according to claim 1, wherein the information processing apparatus is disposed in a first housing separately from the body motion signal detecting apparatus, the body motion signal detecting apparatus includes an information collection section that records the body motion signal information, the information processing apparatus includes an information import section that imports the body motion signal information recorded in the information collection section through communicating means, and the body motion signal information is first stored in the information collection section, and then the body motion signal information is transmitted to the information import section of the information processing apparatus through the communicating means.

6. The information processing method for the body motion signal according to claim 1, wherein the information processing apparatus is disposed in a first housing separately from the body motion signal detecting apparatus, and the true cycle is transmitted to the subject through the body motion signal detecting apparatus.

7. The information processing method for the body motion signal according to claim 1, wherein the repetitive rhythmic motion is a gait.

8. The information processing method for the body motion signal according to claim 1, wherein a severity of Parkinson's disease is evaluated from the true cycle.

9. An information processing system for a body motion signal, the information processing system comprising:

a body motion signal detecting apparatus that detects body motion signal information by a body motion signal detection section that measures non-invasively and continuously at least a repetitive rhythmic motion of a human body of a subject by an operation in which the subject carries the body motion signal detection section and outputs a body motion signal including the body motion signal information, the body motion signal detection section being mounted on, connected to, or housed on the subject;

an information processing apparatus including a central processing unit or a microprocessor implemented to accept the body motion signal and perform information processing on the body motion signal information obtained in the body motion signal detecting apparatus and extracts a result obtained by the information processing, the information processing apparatus including:

a cycle candidate extraction section that applies a pattern matching process on the body motion signal information to extract a rhythm cycle candidate wave as rhythm cycle candidates related to the rhythmic motion;

an auxiliary-wave production section that performs −1 or more times integration on the body motion signal information to obtain a motion trajectory, determines a time scale from the motion trajectory, and that performs coarse-graining on the motion trajectory by using the time scale of the motion trajectory to produce an auxiliary wave; and a cycle selection section that superimposes, by implementing the superimposing on the central processing unit or the microprocessor of the information processing apparatus, the rhythm cycle candidate wave, that was extracted by the cycle candidate extraction section, on the auxiliary wave, that was produced by the auxiliary-wave production section, and selects a cycle of the rhythm cycle candidate wave that has a peak in a region surrounded by a peak of the auxiliary wave, as a true cycle.

10. The information processing system for the body motion signal according to claim 9, wherein
the cycle selection section selects a cycle of the rhythm cycle candidate wave that has a maximum peak in the region surrounded by a peak of the auxiliary wave as the true cycle.

11. The information processing system for the body motion signal according to claim 9, wherein
the information processing apparatus is disposed separately from the body motion signal detecting apparatus,
the body motion signal detecting apparatus includes an information collection section that records the body motion signal information, the information collection section being detachable from the body motion signal detection section, and
the information processing apparatus includes an information import section that imports, for the information processing, the body motion signal information record in the information collection section.

12. The information processing system for the body motion signal according to claim 9, wherein
the body motion signal detecting apparatus and the information processing apparatus are connected to each other through communicating means,
the body motion signal detecting apparatus includes an information collection section that records the body motion signal information, and
the information processing apparatus includes an information import section that imports into the import section the body motion signal information stored in the information collection section via the communicating means.

13. The information processing system for the body motion signal according to claim 9, wherein
the body motion signal detecting apparatus is disposed in a first housing separately from the information processing apparatus, and
the body motion signal detecting apparatus includes a transmission section which transmits the result extracted by the information processing apparatus to the subject.

14. The information processing system for the body motion signal according to claim 9, wherein
the body motion signal detecting apparatus is disposed integrally with the information processing apparatus in a first housing and is configured to be portable with the subject.

15. The information processing system for the body motion signal according to claim 9, comprising
an output section which outputs the result extracted by the information processing apparatus.

16. The information processing system for the body motion signal according to claim 9, comprising
an evaluating apparatus which evaluates a severity of Parkinson's disease from the result extracted by the information processing apparatus.

17. An information processing apparatus including a central processing unit or a microprocessor implemented to perform information processing the information processing apparatus comprising:

an input section that obtains body motion signal information from a body motion signal formed by an operation in which a subject carries a body motion signal detecting apparatus, the body motion apparatus being mounted on, connected to, or housed on the subject and having a body motion signal detection section that measures non-invasively and continuously at least a repetitive rhythmic motion of a human body of the subject;

a cycle candidate extraction section that applies a pattern matching process on the body motion signal information to extract a rhythm cycle candidate wave that is rhythm cycle candidates related to the rhythmic motion;

an auxiliary-wave production section that performs −1 or more times integration on the body motion signal information to obtain a motion trajectory, determines a time scale from the motion trajectory, and that performs coarse-graining on the motion trajectory by using the time scale of the motion trajectory to produce an auxiliary wave; and a cycle selection section that superimposes, by implementing the superimposing on the central processing unit or the microprocessor of the information processing apparatus, the rhythm cycle candidate wave, that was extracted by the cycle candidate extraction section, on the auxiliary wave, that was produced by the auxiliary-wave production section, and selects a cycle of the rhythm cycle candidate wave that has a peak in a region surrounded by a peak of the auxiliary wave, as a true cycle.

18. The information processing apparatus for the body motion signal according to claim 17, wherein
the cycle selection section selects a cycle of the rhythm cycle candidate wave that has a maximum peak in the region surrounded by a peak of the auxiliary wave, as the true cycle.

19. The information processing apparatus for the body motion signal according to claim 17, further comprising:

an evaluation device that evaluates a severity of Parkinson's disease from the true cycle, the evaluation device being attached to the information processing apparatus.

20. A non-transitory computer-readable recording medium which records a program to be used in an information processing method implemented by a central processing unit or a microprocessor to perform information processing including desired process steps, the program causing a computer including the central processing unit or the microprocessor to execute a method comprising:
   obtaining body motion signal information from a body motion signal formed by an operation in which a subject carries a body motion signal detecting apparatus, the body motion signal detection apparatus being mounted on, connected to, or housed on the subject and having a body motion signal detection section that measures non-invasively and continuously at least a repetitive rhythmic motion of a human body of the subject;
   applying a pattern matching process, in a cycle candidate extracting step, on the body motion signal information, and extracting a rhythm cycle candidate wave as rhythm cycle candidates related to the rhythmic motion;
   performing −1 or more times integration, in an auxiliary wave producing step, on the body motion signal information to obtain a motion trajectory, determining a time scale from the motion trajectory, and performing coarse-graining on the motion trajectory by using the time scale of the motion trajectory to produce an auxiliary wave; and
   superimposing, by implementing the superimposing on the central processing unit or the microprocessor in a cycle selecting step, the rhythm cycle candidate wave, that was extracted in the cycle candidate extracting step, on the auxiliary wave, that was obtained in the auxiliary-wave producing step, and selecting a cycle of the rhythm cycle candidate wave which has a peak in a region surrounded by a peak of the auxiliary wave, as a true cycle.

21. The non-transitory computer-readable recording medium according to claim 20, wherein,
   the computer is caused to execute the cycle selecting step in which a cycle of the rhythm cycle candidate wave which has a maximum peak in the region surrounded by a peak of the auxiliary wave is selected as the true cycle.

22. A body motion signal detecting apparatus which is to be used in the information processing method for the body motion signal as defined in claim 1.

23. A method of detecting a body motion signal for obtaining a body motion signal to be used in the information processing method for the body motion signal as defined in claim 1.

24. An outputting apparatus which is used for outputting the true cycle obtained by the information processing method for the body motion signal as defined in claim 1.

25. An outputting method for outputting the true cycle obtained by the information processing method for the body motion signal as defined in claim 1.

26. A diagnosing method of diagnosing an illness using an information processing apparatus including a central processing unit or a microprocessor implemented to perform information processing, the information processing including steps of:
   obtaining body motion signal information from a body motion signal formed by an operation in which a subject carries a body motion signal detecting apparatus, the body motion signal detection apparatus being mounted on, connected to, or housed on the subject and having a body motion signal detection section that measures non-invasively and continuously at least a repetitive rhythmic motion of a human body of the subject;
   applying a pattern matching process, in a cycle candidate extracting step, on the body motion signal information, and extracting a rhythm cycle candidate wave as rhythm cycle candidates related to the rhythmic motion;
   performing −1 or more times integration, in an auxiliary wave producing step, on the body motion signal information to obtain a motion trajectory, determining a time scale from the motion trajectory, and performing coarse-graining on the motion trajectory by using the time scale of the motion trajectory to produce an auxiliary wave; and
   superimposing, by implementing the superimposing on the central processing unit or the microprocessor of the information processing apparatus in a cycle selecting step, the rhythm cycle candidate wave, that was extracted in the cycle candidate extracting step, on the auxiliary wave, that was obtained in the auxiliary wave producing step, and selecting a cycle of the rhythm cycle candidate wave which has a peak in a region surrounded by a peak of the auxiliary wave, as a true cycle.

27. The diagnosing method according to claim 26, wherein the illness is any one of Parkinson's disease, stroke, spinal cord injury, cerebral palsy, myelodysplasia, muscular dystrophy, osteoarthritis, rheumatoid arthritis, multiple sclerosis, alcoholic intoxication, dementia, and hydrocephalus.

28. The diagnosing method according to claim 26, wherein the illness is Parkinson's disease, and
   a severity of Parkinson's disease is evaluated from the true cycle.

29. A diagnosing system for diagnosing an illness, the diagnosing system comprising:
   a body motion signal detecting apparatus that detects body motion signal information by a body motion signal detection section that measures non-invasively and continuously at least a repetitive rhythmic motion of a human body of a subject by an operation in which the subject carries the body motion signal detection section and outputs a body motion signal including the body motion signal information, the body motion signal detection section being mounted on, connected to, or housed on the subject; and
   an information processing apparatus including a central processing unit or a microprocessor implemented to accept the body motion signal and perform information processing on the body motion signal information obtained in the body motion signal detecting apparatus, the information processing apparatus including:
   a cycle candidate extraction section that applies a pattern matching process on the body motion signal information to extract a rhythm cycle candidate wave as rhythm cycle candidates related to the rhythmic motion;
   an auxiliary-wave production section that performs −1 or more times integration on the body motion signal information to obtain a motion trajectory, determines a time scale from the motion trajectory, and that performs coarse-graining on the motion trajectory by using the time scale of the motion trajectory to produce an auxiliary wave; and
   a cycle selection section that superimposes, by implementing the superimposing on the central processing unit or the microprocessor of the information processing apparatus, the rhythm cycle candidate wave, that was extracted by the cycle candidate extraction section, on the auxiliary wave, that was produced by the auxiliary-wave production section, and selects a cycle of the rhythm cycle candidate wave that has a peak in a region surrounded by a peak of the auxiliary wave, as a true cycle.

30. The diagnosing system according to claim 29, wherein the illness is any one of Parkinson's disease, stroke, spinal cord injury, cerebral palsy, myelodysplasia, muscular dystrophy, osteoarthritis, rheumatoid arthritis, multiple sclerosis, alcoholic intoxication, dementia, and hydrocephalus.

31. The diagnosing system according to claim 29, wherein the illness is Parkinson's disease, and
the diagnosing system includes an evaluating apparatus which evaluates a severity of Parkinson's disease from the true cycle.

32. A diagnosing apparatus for diagnosing an illness including a central processing unit or a microprocessor, the diagnosing apparatus comprising:
an input section that obtains body motion signal information from a body motion signal formed by an operation in which a subject carries a body motion signal detecting apparatus, the body motion signal detection apparatus being mounted on, connected to, or housed on the subject and having a body motion signal detection section that measures non-invasively and continuously at least a repetitive rhythmic motion of a human body of the subject;
a cycle candidate extraction section that applies a pattern matching process on the body motion signal information to extract a rhythm cycle candidate wave as rhythm cycle candidates related to the rhythmic motion;
an auxiliary-wave production section that performs −1 or more times integration on the body motion signal information to obtain a motion trajectory, determines a time scale from the motion trajectory, and which performs coarse-graining on the motion trajectory by using the time scale of the motion trajectory to produce an auxiliary wave; and
a cycle selection section that executes a program with the central processing unit or the microprocessor of the diagnosing apparatus to superimpose the rhythm cycle candidate wave, that was extracted by the cycle candidate extraction section, on the auxiliary wave, that was produced by the auxiliary-wave production section, and to select a cycle of the rhythm cycle candidate wave that has a peak in a region surrounded by a peak of the auxiliary wave, as a true cycle.

33. The diagnosing system according to claim 29, wherein the repetitive rhythmic motion is a gait.

34. The diagnosing apparatus according to claim 32, wherein
the repetitive rhythmic motion is a gait,
the illness is Parkinson's disease, and
the diagnosing apparatus includes an evaluating apparatus which evaluates a severity of Parkinson's disease from the true cycle.

35. The information processing method for the body motion signal according to claim 1, further comprising a step of outputting a result obtained by information processing including the steps of applying the pattern matching, performing −1 or more times integration, and superimposing the rhythm cycle candidate wave.

36. The information processing method for the body motion signal according to claim 1, further comprising a step of displaying a result obtained by information processing including the steps of applying the pattern matching, performing −1 or more times integration, and superimposing the rhythm cycle candidate wave.

37. The diagnosing method according to claim 26, further comprising a step of outputting a result obtained by information processing including the steps of applying the pattern matching, performing −1 or more times integration, and superimposing the rhythm cycle candidate wave.

38. The diagnosing method according to claim 26, further comprising a step of displaying a result obtained by information processing including the steps of applying the pattern matching, performing −1 or more times integration, and superimposing the rhythm cycle candidate wave.

* * * * *